US006996472B2

(12) United States Patent
Wilkes et al.

(10) Patent No.: US 6,996,472 B2
(45) Date of Patent: Feb. 7, 2006

(54) DRIFT COMPENSATION METHOD FOR FINGERPRINT SPECTRA

(75) Inventors: Jon G. Wilkes, Little Rock, AR (US); Fatemeh Rafii, White Hall, AR (US); Katherine L. Glover, Nashville, TN (US); Manuel Holcomb, Carlisle, AR (US); Xiaoxi Cao, Redfield, AR (US); John B. Sutherland, White Hall, AR (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 294 days.

(21) Appl. No.: 09/975,530

(22) Filed: Oct. 10, 2001

(65) Prior Publication Data

US 2002/0138210 A1   Sep. 26, 2002

Related U.S. Application Data

(60) Provisional application No. 60/239,549, filed on Oct. 10, 2000.

(51) Int. Cl.
G01N 33/48 (2006.01)
C12P 21/00 (2006.01)
(52) U.S. Cl. ............... 702/19; 435/70.1; 435/71.1
(58) Field of Classification Search ............ 435/29, 435/70.1, 71.1; 702/19
See application file for complete search history.

(56) References Cited

U.S. PATENT DOCUMENTS 5,593,883 A * 1/1997 Cano et al. ............ 435/252.1
5,946,640 A    8/1999 Goodacre et al.
6,087,182 A * 7/2000 Jeng et al. ................ 436/66

OTHER PUBLICATIONS

Acheson et al., Infection and Immunity, vol. 63, pp. 1098-1104, 1993.*
Cebolla et al., Applied and Environmental Microbiology, vol. 61, No. 2, pp. 660-668, 1995.*
Brondz et al., "Multivariate Analyses of Cellular Fatty Acids in Bacteroides, Prevotella, Porphyromonas, Wolinella, and Campylobacter spp.," *Journal of Clinical Microbiology* 29 (1):183-189 (1991).
Mukwaya et al., "Subgrouping of Pseudomonas cepacia by Cellular Fatty Acid Composition," *Journal of Clinical Microbiology* 27(12):2640-2646 (1989).
Jantzen et al., "Hydroxy-Fatty Acid Profiles of Legionella Species: Diagnostic Usefulness Assessed by Principal Component Analysis," *Journal of Clinical Microbiology* 31(6):1413-1419 (1993).

Leonard et al., "Comparison of MIDI Sherlock System and Pulsed-Field Gel Electrophoresis in Characterizing Strains of Methicillin-Resistant *Staphylococcus aureus* from a Recent Hospital Outbreak," *Journal of Clinical Microbiology*, 33(10):2723-2727 (1995).
Olsen et al., "Multivariate Chemosystemactics Demonstrate Two Groups of Actinobacillus actinomycetemcomitans Strains," *Oral Microbiology and Immunology* 8:129-133 (1993).
Sockalingum et al., FT-IR Spectroscopy as an Emerging Method for Rapid Characterization of Microorganisms, *Cellular and Molecular Biology* 44(1):261-269 (1998).
Dykes et al., "Taxonomy of Lactic Acid Bacteria Associated with Vacuum-Packaged Processed Meat Spoilage by Multivariate Analysis of Cellular Fatty Acids," *International Journal of Food Microbiology* 28:89-100 (1995).
Langworthy et al., "Genotypic and Phenotypic Responses of a Riverine Microbial Community to Polycyclic Aromactic Hydrocarbon Contamination," *Applied and Environmental Microbiology* 64(9):3422-3428 (1998).
Couto et al., "Random Amplified Polymorphic DNA and Restriction Enzyme Analysis of PCR Amplified rDNA in Taxonomy: Two Indentification Techniques for Food-Borne Yeasts," *Journal of Applied Bacteriology* 79:525-535 (1995).
Nilsson et al., "Classification of Species in the Genus *Penicillium* by Curie Point Pyrolysis/Mass Spectrometry Followed by Multivariate Ananlysis and Artifical Neural Newtorks," *Journal of Mass Spectrometry* 31:1422-1428 (1996).
Darland, "Principal Component Analysis of Infraspecific Variation in Bacteria," *Applied Microbiology* 30(2):282-289 (1975).
Olsen et al., "Genomic Relationships Between Selected Phage Types of *Salmonella enterica* Subsp. enterica Serotype Typhimurium Defined by Ribotyping, IS200 Typing and PFGE," *Micrbiology* 143:1471-1479 (1997).
Itoh et al., "Cellular Fatty Acids and Aldehydes of Oral Eubacterium," *Federation of European Microbiological Societies* (*Microbiology Letters*) 126:69-74 (1995).

(Continued)

*Primary Examiner*—Ardin H. Marschel
*Assistant Examiner*—Cheyne D. Ly
(74) *Attorney, Agent, or Firm*—Klarquist Sparkman, LLP

(57) ABSTRACT

Methods of compensating for drift in fingerprint spectra of microorganisms caused by changes in their environment are disclosed. These methods of compensating for drift permit identification of microorganisms from their fingerprint spectra regardless of the environment from which the microorganisms are obtained. Furthermore, the disclosed methods may be used to construct coherent databases of fingerprint spectra that may be expanded even though the standard database conditions are no longer experimentally achievable. In particular embodiments, methods of compensating for drift in pyrolysis mass spectra, constructing coherent pyrolysis mass spectral databases, and identifying bacteria from their pyrolysis mass spectra are disclosed.

25 Claims, 16 Drawing Sheets

OTHER PUBLICATIONS

Brosch et al., "Pulsed-Field Fingerprinting of Listeriae: Identification of Genomic Divisions for Listeria monocytogenes and Their Correlation with Serovar," *Applied and Environmental Microbiology* 60(7):2584-2592 (1994).

Wilkes et al., "Feasibility of Assembling A Pyrolysis Mass Spectrometric Library for Rapid Chemotaxonomy of Microbial Samples," Pittsburgh Conference 2000, Book of Abstracts, Mar. 12-17, 2000, New Orleans, Poster 1936P.

Atalan et al., "Artifical Neural Network Analysis of Pyrolysis Mass Spectrometric Data in the Identification of Streptomyces Strains," *FEMS Microbiology Letters* 107: 321-326 (1993).

Goodacre et al., "Correction of Mass Spectral Drift Using Artificial Neural Networks," *Anal. Chem.* 68:271-280 (1996).

* cited by examiner

DRIFT COMPENSATION METHOD FOR FINGERPRINT SPECTRA

CROSS-REFERENCE TO RELATED APPLICATIONS

This application claims priority from provisional Patent Application No. 60/239,549, filed Oct. 10, 2000, the entirety of which is incorporated by reference herein.

FIELD

Disclosed are methods of quickly identifying microorganisms, especially database methods for identifying microorganisms, based upon their spectroscopic, spectrometric and chromatographic characteristics regardless of the environment from which the microorganisms are obtained.

BACKGROUND

Chemotaxonomy of microorganisms based upon their spectroscopic, spectrometric, and chromatographic characteristics represents a useful method for the identification of microorganisms such as yeast, fungi, protozoa, and bacteria. Typically, such chemotaxonomic methods are based upon instrumental methods that provide "fingerprint" spectra or chromatograms (i.e., spectra or chromatograms that are unique to each type of microorganism). Such fingerprinting methods include mass spectrometric methods (for example, pyrolysis mass spectrometry), infrared spectroscopy, ion mobility spectrometry, gas chromatography, liquid chromatography, nuclear magnetic resonance, and various hyphenated techniques such as gas chromatography-mass spectrometry (GC-MS) and high performance liquid chromatography-Fourier transform infrared spectroscopy (HPLC-FTIR).

Unfortunately, instrumental fingerprinting methods, such as pyrolysis mass spectrometry, tend to suffer from irreproducibility due to both instrumental and environmental factors. For example, continued use of a mass spectrometer leads to contamination of the ion optics and thus can lead to alterations in the appearance of a microorganism's fingerprint mass spectrum. Changes in a microorganism's characteristics due to environmental factors, such as a change in the growth medium used to culture the microorganism, can also alter the appearance of its fingerprint spectrum. Irreproducibility of spectral data due to instrumental and environmental sources makes it difficult to classify or identify microorganisms based on fingerprint spectral patterns. On the other hand, instrumental fingerprinting methods are much more rapid than traditional methods of identifying microorganisms and they hold great potential for detection and identification of biological warfare agents and rapid identification of pathogenic microorganisms in outbreak situations.

SUMMARY OF THE DISCLOSURE

Disclosed are methods that are capable of compensating for both instrumental and environmental drift in fingerprint spectra. Furthermore, such methods make it possible to construct coherent databases useful for identification of microorganisms based upon their fingerprint spectral data.

DETAILED DESCRIPTION OF THE DISCLOSED EMBODIMENTS

Abbreviations and Definitions

Figure 1:
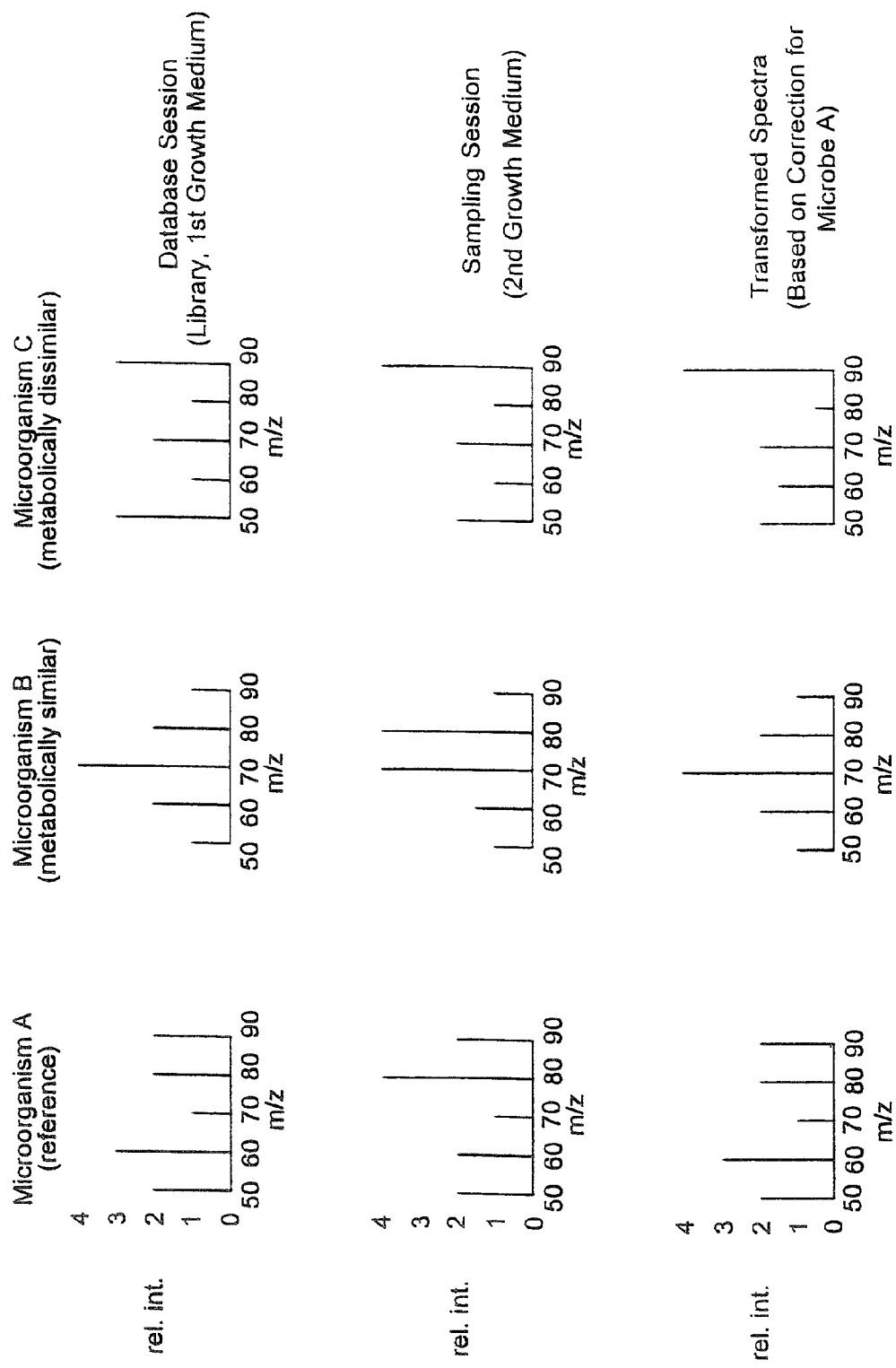
FIG. 1 is diagram showing hypothetical fingerprint spectra for three different microorganisms cultured on two different growth media. Also shown are transformed fingerprint spectra for each microorganism that were produced using a correction algorithm derived from the relationship between the fingerprint spectra of the reference microorganism grown on the two different growth media.

FTIR—Fourier-transform Infrared Spectroscopy
ATR-FTIR—Attenuated Reflectance Fourier-transform Infrared Spectroscopy
TSA—tryptic soy agar
TCBS—thiosulfate citrate bile source The singular forms "a", "an", and "the" refer to one or more, unless the context clearly dictates otherwise.

"Comprises" means including.

"Comprising A or B" means including A or B, or A and B, unless the context clearly indicates otherwise.

Environment—the chemical and physical surroundings of an organism. In some instances the chemical and physical surroundings may be mediated by biological factors such as the presence of other microorganisms.

Environmental factors (conditions)—the chemical and physical parameters that characterize an environment. Environmental factors include stimuli that affect the metabolic state of an organism. Such factors also include the identity and/or concentration of the chemical (organic and inorganic) constituents (such as sugars, salts, amino acids, antibiotics, buffers, pH) which comprise the substrate (e.g. a microbial growth medium) supporting growth of an organism, and temperature. Environmental factors further include pressure, presence of other organisms, exposure to light, humidity, and exposure to gases, such as oxygen.

Principal Component (PC)—Principal component analysis is a mathematical manipulation of a data matrix where the goal is to represent the variation present in many variables using a small number of 'factors.' A new row space in constructed in which to plot the samples by redefining the axes using factors rather than the original measurement variables. These new axes, referred to as factors or principal components (PCs), allow the analyst to probe matrices with many variables and to view the true multivariate nature of data in a relatively small number of dimensions. (K. S. Beebe, R. J. Pell, and M. B. Seasholtz *Chemometrics: a practical guide,* John Wiley & Sons: New York. 1998, pp. 81–82). The first principal component (PC1) explains the maximum amount of variation possible in the data set in one direction: it lies in the direction of maximum spread of data points. The second principal component (PC2), defined as orthogonal to (and independent from) the first, explains the maximum variation possible using the remaining variations not explained in PC1. Each sample will have one co-ordinate (called a score) along each of the new PCs. Therefore, the sample can be located on a 2-dimensional PC Score Plot using the two co-ordinates of the two selected PCs. Consider a data set comprised of 30 samples, 3 each from ten groups (such as ten different bacterial strains), in which each sample is represented by 800 original measurement variables (such as m/z units in a mass spectrum). Depending on the inherent dimensionality of the set, it would be possible to calculate up to 30 PCs. In all likelihood, not all of these 30 would represent statistically significant variations. The dimensionality required to represent the data can be further reduced by calculating Canonical Variates (CVs, described below). In this calculation using fewer than the 30 PCs can eliminate some of the statistically insignificant variation ("noise"). For mass spectral data sets one typically uses enough PCs to account for 85–95% of the original variance.

Canonical variate (CV)—CV vectors are orthogonal, linear combinations of principal components (PCs, see definition). Like PCs, CVs are ranked in the order of decreasing residual variance. Unlike PCs, CVs reflect the identity of separate groups of samples in the data set. The first CV vector is calculated as a linear combination of selected PCs that maximizes the variance between distinct groups of data. The 2nd CV, orthogonal to the first, is based on residual variance not incorporated into the 1st CV. In a particular data set, the maximum number of CVs is one less than the number of distinct groups. Each sample in a data set will have a co-ordinate (called a score) associated with each CV. Therefore, the sample can be located on a 2-dimensional CV Score Plot using the two co-ordinates of the two selected CVs. Samples having similar scores appear near each other on the CV score plot. Samples from different groups may have similar scores in the first two CVs but different scores in the higher number CV space. Therefore, in using CV vectors to identify metabolically similar microorganisms, the number of groups of microorganisms examined on a single plot may be three to six, rather than ten to twenty, to enable visual examination while incorporating most of the significant available variance.

Score Plot—For either PCs or CVs each sample has a co-ordinate in the multidimensional space defined by that vector. A score plot is typically a plot of two selected PCs or CVs in which the sample symbol is located on the plot using its corresponding co-ordinates.

Coherent Database—a database of fingerprint spectra in which additional fingerprint spectra of microorganisms may be added to the database, even though they are not measured under identical instrumental and environmental conditions. Spectra added to such a database are algorithmically transformed to compensate for any changes in instrumental and environmental conditions that occur after initial establishment of the database. Therefore, the database remains "coherent" even as it grows.

Between-sessions drift—drift due to changes in either instrumental or environmental factors that occur, for example, because of changes in the operating parameters of an instrument when it is either restarted or re-calibrated or when there are changes in the growth medium used to culture a sample of microorganisms. This term is for drift occurring between separate data gathering events.

Within-session drift—drift due to changes in an instrument's sensitivity and resolution as the instrument is continually run in a single data gathering event. This term includes drift due to the electronics of an instrument as a function of their temperature and due to contamination of instrumental components during a data-gathering event.

Microorganism—a microscopic organism, including bacteria (e.g. gram positive and gram negative cocci and gram positive and gram negative bacilli, mycoplasmas, rickettsias, actinomycetes, and archaeobacteria), fungi (fungi, yeast, molds), and protozoa (amoebae, flagellates, ciliates, and sporozoa). While viruses (naked viruses and enveloped viruses) and prions are not minute "living" organisms as typically ascribed to the term microorganism, for purposes of this disclosure they are included in the term microorganism because of their effect on biological systems. The term microorganism also encompasses quiescent forms of microscopic organisms such as spores (endospores). Certain microorganisms are pathogens.

Microorganism of interest—in some embodiments the microorganism of interest is a microorganism for which an identity (such as its genus, species, or strain) has not yet been established but for which this information is desired. An example of a microorganism of interest would be a pathogen isolated from a subject for whom a microbiological diagnosis is desired to initiate therapy. In other embodiments, the microorganism of interest is a microorganism for which an identity has been established, but for which a relationship to other microorganisms has not yet been established. An example of such a relationship is whether the microorganism is of the same genus, species, or strain as another microorganism.

Pathogen—a specific causative agent of disease, such as a bacterium, virus, fungus, protozoan, or prion.

Fingerprint spectra (spectrum)—spectra (a spectrum) or chromatograms (a chromatogram) of microorganisms or their chemical constituents that may serve as the basis for distinguishing microorganisms of different taxonomic groups. Physiologically similar groups (e.g. facultatively anaerobic gram negative rods; see, for example, *Bergey's Manual of Determinative Bacteriology*, 9$^{th}$ ed., Williams and Wilkins, Baltimore, Md., 1994), families, genera, species, strains, or sub-strains of microorganisms are examples of such taxonomic groups. Examples of fingerprint spectra include mass spectra [further including but not limited to electron impact, pyrolysis, matrix-assisted laser desorption ionization (MALDI), CI, electrospray ionization (ESI), nanospray, APCI, and metastable atom bombardment (MAB) mass spectra)], infrared spectra (further including but not limited to Fourier-transform infrared spectra, diffuse-reflectance infrared spectra, and attenuated total reflectance infrared spectra), ion-mobility spectra, electrophoretograms, gas chromatograms (further including chromatograms of derivatized cellular fatty acids, sugars, or amino acids), high-performance liquid chromatograms of cellular constituents (such as proteins, nucleic acids, lipids, and sugars), and nuclear magnetic resonance spectra (such as $^{13}C$, $^{1}H$, $^{15}N$, and $^{31}p$ spectra, including two-dimensional homonuclear and heteronuclear magnetic resonance spectra). Fingerprint spectra also include any combination of fingerprint spectra obtained from the techniques listed above. Fingerprint spectra may also be portions or subsets of fingerprint spectra.

Metabolically Similar—As applied to microorganisms, two microorganisms are metabolically similar if they respond to their environment by producing similar sets of biomolecules. Metabolically similar microorganisms will, in some embodiments, belong to a single class of physiologically similar microorganisms (e.g.—facultatively anaerobic gram negative rods or dissimilatory sulfate-reducing bacteria; see, for example, *Bergey's Manual of Determinative Bacteriology*, 9$^{th}$ ed., Williams and Wilkins, Baltimore, Md., 1994, *Food Microbiology: Fundamentals and Frontiers*, Doyle et al., eds., ASM Press, Washington, D.C., 1997, or *Zinsser Microbiology*, 19$^{th}$ ed., Joklik et al., eds., Appleton & Lange, Norwalk, Conn., 1988 for groupings of microorganisms according to their physiological characteristics. Fungi including yeast are characteristically similar if they have similar morphology, ultrastructure, cell wall composition, carbohydrate biochemistry, and polysaccharide biosynthesis. Protozoa, which are identified by their morphological characteristics may be further distinguished by their usual locations. In other embodiments, metabolically similar microorganisms are microorganisms within the same taxonomic family (for example, Enterobacteriaceae), genus (for example, *Escherichia*), species (for example, *Escherichia coli*), strain (for example, *E. coli* 1090) or serotype (e.g.—*E. coli* serotype O:150, a serotype that is particularly pathogenic). Metabolically similar microorganisms are, in other embodiments, organisms that exhibit similar fingerprint spectra that change similarly in response to changes in environment.

Classification parameters—classification parameters include for example gram staining (e.g. gram positive or negative) and morphology (rods or cocci) or oxygen requirements (e.g. aerobic or anaerobic) or other physiological characteristics (such as ability to reduce sulfate). Further examples of classification parameters may be found in *Bergey's Manual of Determinative Bacteriology*, 9$^{th}$ ed., Williams and Wilkins, Baltimore, Md., 1994, *Food Microbiology: Fundamentals and Frontiers*, Doyle et al., eds., ASM Press, Washington, D.C., 1997, and *Zinsser Microbiology*, 19$^{th}$ ed., Joklik et al., eds., Appleton & Lange, Norwalk, Conn., 1988, all of which are incorporated by reference herein.

Growth Medium—any nutrient system for the cultivation of microorganisms that is sometimes a simple substance but more commonly a complex of inorganic and organic materials in a fluid base or one rendered more or less solid by coagulation or by the addition of gelatin or agar and sometimes referred to as a nutrient medium. Such growth media may be non-selective (i.e., they support the growth of a wide variety of microorganisms) or selective (i.e., they support the growth of only particular microorganisms).

Growth Conditions—the physical and chemical parameters of an organism's environment other than those defined by the chemical constituents of the growth medium. For example, growth conditions include the temperature of incubation, exposure to light, and the presence of gases such as oxygen.

Library database growth medium—a growth medium that supports the growth of all the microorganisms in a particular library database.

Test growth medium—any growth medium other than the library growth medium.

Nuclear Magnetic Resonance (NMR)—a phenomenon exhibited by a large number of atomic nuclei in which nuclei in a magnetic field absorb energy from a radio-frequency field at certain characteristic frequencies. Particular examples of nuclei that exhibit this phenomenon include $^{13}C$, $^{1}H$, $^{15}N$, $^{19}F$ and $^{31}p$.

Mass Spectrometry (MS)—a method of chemical analysis in which the substance to be analyzed is placed in a vacuum and reduced to low pressure. The resulting vapor is exposed, for example, to a beam of electrons which causes ionization to occur, either of the molecules or their fragments. The ions thus produced are accelerated and then passed through a mass analyzer that separates the ions according to their mass-to-charge ratio.

Electron Impact Mass Spectrometry (EI MS)—a mass spectrometric technique in which the ionization of molecules and their fragments is accomplished by a beam of electrons that impacts the molecules and their fragments. Typically, as the energy of the electron beam is increased, the number of fragments produced from a molecule increases.

Metastable Atom Bombardment (MAB)—a technique for ionizing analyte molecules for mass spectral analysis by impacting analyte molecules with metastable atoms in the gas phase. Metastable atoms are typically generated in a noble gas discharge plasma (for example, helium, neon, argon, krypton, and xenon discharge plasmas) although a molecular nitrogen, $N_2$, plasma has also been found useful in many applications.

Pyrolysis Mass Spectrometry (PyMS)—a mass spectrometric technique in which samples are subjected to a controlled thermal degradation in an inert atmosphere or vacuum (pyrolysis). This converts the chemical constituents that make up the sample into low molecular weight volatile compounds. Pyrolysis mass spectrometry is a method that measures the masses and abundances of these volatile fragments.

Infrared Spectroscopy (IR)—an analytical technique which measures a range of wavelengths (or frequencies), in the infrared region or near-infrared region of the electromagnetic spectrum, that are absorbed by a specimen and are characteristic of the specimen's molecular constitution. Infrared absorption bands identify molecular structure components, such as aromatic, olefin, aliphatic, aldehyde, ketone, carboxylic acid, alcohol, amine, and amide groups. The frequency at which absorption occurs also reflects the frequency at which the bonds in these components stretch and and/or bend. Variants of the technique include Fourier-transform IR spectroscopy (FTIR) and diffuse reflectance IR spectroscopies, for example, attenuated total reflectance Fourier-transform IR spectroscopy (ATR-FTR).

Chromatography—any number of analytical techniques wherein sample molecules are separated by differential interactions with a stationary phase as they are carried past the stationary phase in a mobile phase. The differential interactions that provide for chromatographic separation depend upon the chemical and physical properties of the sample molecules, the stationary phase, and the mobile phase. As sample molecules are carried along by the mobile phase they interact with the stationary phase. If a molecule interacts more strongly with the stationary phase by virtue of its chemical and physical properties (which are a function of its structure), it will spend less time moving with the mobile phase and will take longer to traverse the stationary phase. A chromatogram is a plot of the time it takes the various constituents of a sample to traverse the stationary phase. Chromatographic techniques may be differentiated based upon the state of matter comprising the mobile phase. If the mobile phase is a gas, the technique is gas chromatography. If the mobile phase is a liquid, the technique is liquid chromatography. If the mobile phase is a super-critical fluid, the technique is super-critical fluid chromatography.

Transformation (transform)—Application of a relationship between two fingerprint spectra (or portions thereof) measured under two different sets of conditions (environmental and/or instrumental), in order to convert one fingerprint spectrum (or portion thereof) to the other (or portion thereof), is referred to herein as the act of transformation. Transformation also includes the act of applying a relationship derived between two fingerprint spectra (or portions thereof) of one microorganism to fingerprint spectra (or corresponding portions thereof) of other microorganisms (metabolically similar or not).

Library Database—a database of fingerprint spectra that are obtained from microorganisms grown on a growth medium that is capable of sustaining growth of all the microorganism that are included in the database.

In one aspect of the disclosure, methods of compensating for changes in the fingerprint spectra of microorganisms that are due to changes in the microorganism's environment are disclosed. These methods are based in part on the similar fingerprint spectra of metabolically similar microorganisms under similar environmental conditions and the similar changes observed in the fingerprint spectra of metabolically similar microorganisms in response to similar changes in environmental conditions.

That the fingerprint spectra of two metabolically similar microorganisms are similar under similar environmental conditions and undergo similar changes in response to similar changes in environment can be understood by considering how a microorganism interacts with its environment. In a given environment, a microorganism will produce a set of biomolecules that furthers, to the extent possible, the existence of the microorganism in that environment. When the chemical and physical attributes of its environment change a microorganism will respond by producing a new set of biomolecules. For example, the microorganism may produce metabolic enzymes and structural proteins that enable the microorganism to utilize newly available nutrients and/or serve to protect the microorganism from any toxic chemical constituents or harmful physical attributes of the new environment. If two microorganisms are metabolically similar, the biomolecules they produce in response to environmental factors will tend to be similar. On the other hand, metabolically dissimilar microorganisms will activate different metabolic pathways and produce dissimilar sets of biomolecules in response to their environment.

Because fingerprint spectra of microorganisms reflect the identities and relative concentrations of biomolecules in microorganisms, the fingerprint spectra of metabolically similar microorganisms are typically similar in a given environment and change similarly in response to changes in the environment. Conversely, fingerprint spectra of metabolically dissimilar microorganisms tend not to be similar in a particular environment and change in disparate ways as the environment changes.

In some examples, methods for identifying metabolically similar microorganisms are disclosed. Metabolically similar microorganisms may be identified by the similarity of their fingerprint spectra in one environment. Alternatively, metabolically similar microorganisms may be identified by similar differences in the fingerprint spectra between two or more environments. For example, after measuring a fingerprint spectrum of a microorganism obtained from a first environment and measuring a fingerprint spectrum of the microorganism obtained from a second environment, differences between the fingerprint spectra obtained from the two environments may be detected. These differences may then be compared to the differences observed in the fingerprint spectra of other microorganisms between the first and second environments. In one disclosed embodiment, the fingerprint spectra of two or more microorganisms from each of two or more environments are analyzed by statistical pattern recognition and represented in canonical variate (CV) and/or principal component (PC) space. Each fingerprint spectrum is described by a set of coordinates in CV and PC space. Proximity of spectra in CV or PC space is indicative of similar fingerprint spectra and also of metabolic similarity if the spectra are for microorganisms from the same or similar environments. Metabolic similarity of microorganisms may also be detected by comparing vectors in CV or PC space that are determined between a microorganism's fingerprint spectrum in a first environment and its spectrum in a second environment. Such vectors contain information about how the spectra of microorganisms change between two environments. In a more particular disclosed embodiment, fingerprint spectra of two or more microorganisms from two or more environments are located on a two-dimensional CV score plot and vectors between the microorganism' spectra in a first environment and a second environment are determined. Metabolic similarity between microorganisms is indicated by similarity in the direction and magnitude of these vectors in two-dimensional CV space.

The relationship of a microorganism's fingerprint spectrum in a first environment to its fingerprint spectrum in a second environment may be applied to transform the microorganism's fingerprint spectrum in the first environment to its fingerprint spectrum in the second environment and vice versa. Because metabolically similar microorganisms undergo similar changes in response to a change in environment, the relationship derived for a first microorganism between two environments may be applied to successfully transform the spectra of other metabolically similar microorganisms between two identical or similar environments. Therefore, in certain examples, methods of compensating for environmental drift in fingerprint spectra are disclosed. In one embodiment, the fingerprint spectra of one or more microorganisms obtained from two environments are used to compensate for environmentally induced drift in the fingerprint spectra of other metabolically similar microorganisms between the two environments.

In another particular example, methods are disclosed of compensating for environmental drift in the fingerprint spectra of microorganisms caused by changes in the way the microorganisms are cultured (for example, changes in the growth medium and/or growth conditions) are disclosed. In one example, such methods involve culturing, in a first environment, a microorganism of interest and a second microorganism that is presumably metabolically similar to the microorganism of interest. A fingerprint spectrum of the microorganism of interest cultured in the first environment and a fingerprint spectrum of the second microorganism cultured in the first environment are measured. Differences between the fingerprint spectrum of the second microorganism cultured in the first environment and its fingerprint spectrum in the second environment are determined. The differences observed in the fingerprint spectra of the second microorganism between the first and second environments are applied to transform the fingerprint spectrum of the microorganism of interest into a fingerprint spectrum that would be expected had the microorganism of interest actually been cultured in the second environment.

In another example, a microorganism of interest may be identified by measuring its fingerprint spectrum in a first environment, transforming its fingerprint spectrum in the first environment to an expected fingerprint spectrum in a second environment using the relationship(s) between the fingerprint spectra of one or more metabolically similar microorganisms between the first and second environments, and comparing the expected fingerprint spectrum for the microorganism of interest in the second environment to the spectra of known microorganisms in the second environment. In a particular embodiment, the expected spectrum of a microorganism of interest in a standard database environment is compared, such as by pattern recognition, to the fingerprint spectra of known microorganisms in the standard database environment and identified by the similarity of its expected fingerprint spectrum to the fingerprint spectrum of a previously identified microorganism in the database.

The ability to correct for environmental drift in the fingerprint spectra of one microorganism by using the fingerprint spectra of other, metabolically similar microorganisms reduces the time necessary to identify microorganisms based upon their fingerprint spectra. It also permits construction of coherent fingerprint spectral databases that may be referenced to identify microorganisms. Thus, in another aspect, methods for constructing coherent microbial fingerprint spectral databases are disclosed.

EXAMPLES

In one example, the disclosed methods are based upon the discovery that it is possible to correct drift (instrumental and environmental) in the fingerprint spectra of a plurality of metabolically similar microorganisms by reference to fingerprint spectra of a single microorganism within that plurality of metabolically similar microorganisms. For example, it has been found that an algorithm that corrects one microorganism's fingerprint spectrum for instrumental drift (e.g. that caused by electronic drift, contamination, or a change in operating conditions) and environmental drift (e.g. a change in growth medium) may be applied with success to transform the fingerprint spectra of other metabolically similar microorganisms.

The discovery that corrections used to transform one microorganism's fingerprint spectrum can be applied to metabolically similar microorganisms makes it possible to construct a coherent library database of fingerprint spectra (i.e., a database where fingerprint spectra of microorganisms can be used to identify microorganisms and additional fingerprint spectra of microorganisms may be added to the database, even though they are not measured under identical instrumental and environmental conditions). For example, fingerprint spectra of new strains of *E. coli* that are cultured on a particular growth medium may be added to the database (established using a different growth medium) at any time. This may be accomplished by measuring the fingerprint spectra of the new strains in the same session (sampling session) as a reference strain of *E. coli* that is already in the database and exhibits similar metabolic characteristics (for example, the ability to metabolize a particular antibiotic). The relationship between the database fingerprint spectrum of the reference strain and the fingerprint spectrum measured in the same session as the new strains may then be utilized to derive an algorithm that transforms the reference strain's sampling session fingerprint spectrum into its database fingerprint spectrum. This same algorithm may then be used to transform the sampling session fingerprint spectra of the strains not currently in the database into fingerprint spectra that may be added as if they were measured during the establishment of the database.

The discovery also makes it possible to measure fingerprint spectra of unknown microorganisms concurrently with only a few reference microorganisms (genus, species or strains) rather than a reference for each of the microorganisms that may be found in a particular sample. For example, by choosing sets of reference microorganisms that include representatives of each of the groups of metabolically similar microorganisms that presumably may be found in a particular sample, the need to concurrently measure fingerprint spectra of all the microorganisms that might possibly be within the particular sample is obviated and time and effort are saved. Alternatively, including only the major anticipated pathogenic strains as references may reduce the number of reference species required for spectral transformation. In this case, when an unknown microorganism does not appear to have an appropriate, metabolically similar reference on which to base a transformation it is probably not toxicologically significant. Once one or more appropriate, metabolically similar reference microorganism are identified, their spectra may be used to generate transformation algorithms that may then be applied to the fingerprint spectra of metabolically similar unknown microorganisms to generate expected fingerprint spectra for the unknown microorganisms. Such transformed fingerprint spectra represent fingerprint spectra the unknowns would be expected to exhibit if the unknowns had actually been grown on the library database growth medium. Such transformed fingerprint spectra may then be directly compared to database fingerprint spectra (visually or by pattern recognition means) for identification of the unknown microorganisms.

The ability to transform fingerprint spectra of microorganisms grown on growth media (e.g. selective growth media) different from the growth medium used to generate a database (library growth medium) into their database equivalents may also serve to reduce the time needed to identify a microorganism. Reducing the time needed to identify a microorganism is especially useful in a microbial outbreak situation. For example, if the clinical signs and symptoms exhibited by one or more patients suggest that the microorganism responsible for an outbreak may be of the genera, *Escherichia*, *Shigella*, or *Salmonella*, samples obtained from the patient's gastric contents or from presumably contaminated food or water are typically cultured on a selective growth medium to quickly eliminate interfering bacteria. A significant amount of time is saved by not having to re-grow unknown microorganisms (grown on the selective growth medium) on a library database growth medium before measuring their fingerprint spectra for identification. Instead, reference species from each of the putative genera may be grown at the same time on the same selective growth medium used to isolate the unknown microorganism. Fingerprint spectra of the reference microorganisms grown on the selective growth medium may then be obtained concurrently with the unknown's fingerprint spectrum and compared to library database fingerprint spectra of the reference microorganisms. Differences between the two fingerprint spectra for a particular reference microorganism may then be used to transform fingerprint spectra of unknown microorganisms that are metabolically similar to the particular reference microorganism. Once transformed into a fingerprint spectrum that resembles a fingerprint spectrum which presumably would have been obtained if the unknown microorganisms had been grown on the library database growth medium, the transformed fingerprint spectrum may be compared to a database of such fingerprint spectra to identify the unknown microorganism responsible for the outbreak. This method may also be extended to the case where the unknown microorganism is isolated directly from its environment and analyzed without a culturing step.

Example 1

Database Construction and Consultation for Microbial Identification

In its various embodiments, the methods presented herein may be utilized for both assembling a coherent database of fingerprint spectra for known microorganisms and consulting such databases for identification and classification of unknown microorganisms. Assembly and consultation of such databases may be automated using a computer implemented software program.

A. Assembly of a Coherent Database

A library database of fingerprint spectra for the identification or taxonomic classification of microorganisms may be compiled using fingerprint spectra (e.g. pyrolysis mass spectra) for microorganisms grown on a non-selective growth medium such as Tryptic Soy Agar (TSA). Other examples of non-selective growth media are Luria-Bertani and blood agar. A non-selective growth medium such as TSA, that supports the growth of numerous types of microorganisms, may be utilized during construction of a library database that includes many different types of microorganisms. However, in outbreak situations the first cultures are commonly obtained on selective growth media for the anticipated species (based on epidemiology and symptomology) in order to reduce the microbial background of irrelevant species. For example, if outbreak symptoms suggest *Vibrio* contamination of seafood (e.g. severe watery diarrhea and vomiting following ingestion of seafood), a sample of the seafood might be introduced into a *Vibrio*-selective growth medium such as thiosulfate citrate bile source (TCBS) to provide a first culture.

A coherent library database allows rapid identification of a microorganism (a problem discussed at more length in section B, below) by making it possible to identify a microorganism based upon a fingerprint spectrum of the microorganism grown on a selective growth medium. For example, a microorganism grown on a *Vibrio*-selective growth medium such as TCBS could be identified by measuring its fingerprint spectrum without having to re-grow the microorganism on the non-selective growth medium used for compilation of the library database. A coherent library database that makes this possible can be used in association with a mechanism for transforming the fingerprint spectrum of a microorganism grown on a selective growth medium into an expected fingerprint spectrum of the microorganism if it were grown on the same non-selective growth medium used for compilation of the library database. Using a transformed fingerprint spectrum, the library database may be consulted to identify the microorganism.

In disclosed embodiments, a coherent library database is assembled by identifying groups of microorganisms that have fingerprint spectra that vary in parallel as a function of changes in growth media constituents (i.e. are metabolically similar).

Microorganisms may be grouped experimentally as follows. First, all of the microorganisms that are to be included in the library database are grown both on a selective growth medium that supports their growth and a less-selective growth medium used for compilation of the library database. Fingerprint spectra for each microorganism grown on each growth medium are measured and the fingerprint spectra are analyzed using a pattern recognition program (e.g. RESolve, Colorado School of Mines, Golden, Colo.) to generate principal components and canonical variates of the data (see, for example, *Computer Assisted Bacterial Systematics*, Goodfellow et al, eds., Academic Press, London, 1985). Following such analysis, each fingerprint spectrum may be represented as a point in multi-dimensional space, where the principal components or canonical variates are the axes of that space. If the microorganisms produce different biomolecules on the two growth media, their fingerprint spectra from the two media will be represented by two points separated in multidimensional space. A vector defined, for example, as connecting the point representing the selective medium fingerprint spectrum of a microorganism to the point representing its spectrum when grown on the less selective library database medium may be determined for each microorganism. Similarities between the directions and the lengths of these vectors may be detected by pattern recognition and the microorganisms grouped according to the similarities of their vectors.

A quantitative measure of vector similarity may be based on the quality of the result: an identification using transformed spectra correctly assigns the highest probability of class identity to the proper library bacterium. For any database, a standard of performance is that the unknown spectrum be most similar to that of the correct bacterium. Even for small databases of spectra obtained in a single session, probabilities of class membership vary a good deal from sample to sample: for good data, from 25% to 100% where other probabilities are near zero. Some groups of replicate spectra are tightly clustered and others more disbursed. Therefore, an appropriate way of demonstrating vector similarity is not by a direct comparison of transform vectors but by the quality of assignment that results from their use.

Groups having functionally equivalent transform vectors represent metabolically similar microorganisms (metabolic similarity groups). By this criterion there may be one or more groups of metabolically similar microorganisms amongst those in the library database.

During construction of the database, a large batch of non-selective growth medium such as TSA would typically be purchased and preserved for future use as the library database growth medium so that as new microorganisms are isolated and become available they may be cultured and have their library database fingerprint spectra determined. By using the same batch of growth medium for all database fingerprint spectra, variations in the fingerprint spectra due to differences in the nutrient profile between batches is eliminated. However, before entering each fingerprint spectrum into the database, fingerprint spectra using the standard TSA, even if obtained on different instruments or on the same, re-tuned instrument, are transformed to an expected spectrum under arbitrarily specified standard conditions using a spectral compensation algorithm based upon an appropriate reference microorganism. In this case, there is no significant contribution to variation arising from environmental factors, so the algorithm corrects instrumental drift only.

More examples of fingerprint spectra can be subsequently added to the database. For authenticated strains already in the database, new fingerprint spectra that are to be added to the database would first be transformed using the relationship between the new fingerprint spectra and the previously catalogued fingerprint spectra of the exact strain. New microorganisms, not already in the database, would be grown on the same agar and instrumental drift compensation (as tracked by strains already in the database and analyzed along with the new strains ) would be the only correction necessary because, by using the same standard batch of growth medium, drift due to changes in the growth medium are avoided.

The disclosed methods may also be used to add new microorganisms to the library database even after the preserved batch of library database growth medium is exhausted. In this situation, compensation to the database conditions may be performed based on the fingerprint spectra of metabolically similar microorganisms already in the database as follows. The new microorganism and a representative microorganism from each of the metabolically similar groups identified in the library database are grown both on a selective growth medium and the new batch of library database growth medium. Fingerprint spectra are measured for each microorganism grown on the two growth media. The fingerprint spectra are analyzed by pattern recognition to generate principal components and canonical variates. Vectors are determined between the fingerprint spectra of each microorganism grown on the two growth media. The representative of a metabolically similar group within the library database with a vector that is most similar to the vector determined for the new microorganism is chosen to serve as the basis of compensation for the new microorganism. Once the most similar representative of a metabolically similar group of microorganisms is determined, its fingerprint spectrum from the new batch of library database growth medium is compared to its fingerprint spectrum from the preserved batch of library database growth medium that is now exhausted. The differences between these two fingerprint spectra are used to transform the fingerprint spectrum of the new microorganism into an expected fingerprint spectrum of the new microorganism. The expected fingerprint spectrum represents how the new microorganism's fingerprint spectrum might have looked if it had been measured after growth on the preserved, but now exhausted, library database growth medium. This transformed fingerprint spectrum then is entered into the library database as the new microorganism's library fingerprint spectrum.

Different standard fingerprint spectral databases may be assembled whenever there are major experimental variations, such as significant ionization mode variations, for example, between electrospray MS spectra and EI MS spectra. While the disclosed correction algorithms may work to transform one form of soft MAB ionization spectra to another (argon to nitrogen, for example), optimally, separate libraries would be maintained even if microbial samples were cultured on the same TSA agar. The methods of algorithmic compensation work best in correcting for instrumental drift within and between sessions, for growth medium variations, and for instrument specific variations. Compensation may also be achieved for minor variations associated with different microbial growth times (24 hours versus 20 hours, for example), but optimal results are achieved with less extreme variations in sample growth time.

B. Consultation of the Database for Identification of Unknowns

Unknown microorganisms may be identified using a library database of fingerprint spectra, whether or not the unknown samples are cultured on the library database growth medium. If an unknown microorganism is grown on the library database growth medium, its fingerprint spectrum measured during a particular sampling session may be corrected for changes in instrumental conditions and compared to fingerprint spectra in the library database. Correction for changes in instrumental conditions may be performed using differences between the spectra of representatives of the metabolic similarity groups within library database (also cultured on the library database growth medium) measured during the sampling session and the library database spectra of those representatives. The differences of the representative microorganism with a fingerprint spectrum most similar to the unknown's are used to transform the unknown's fingerprint spectrum to an expected fingerprint spectrum if the unknown had been analyzed under the same conditions that were used to measure the database spectra.

If an unknown microorganism is grown on a growth medium different from the library database growth medium (e.g. a selective growth medium), a representative of each group of metabolically similar microorganisms within the library database that will grow on the same growth medium is cultured. For example, if the samples were grown on a *Vibrio*-selective growth medium such as TCBS, then a representative of each of the metabolically similar groups of microorganisms that will grow on TCBS may be cultured on that growth medium. Fingerprint spectra may then be obtained for the unknown microorganism and the metabolic similarity group representatives grown on TCBS.

The metabolic similarity group representative used as the basis for transforming the unknown microorganism's fingerprint spectrum into an expected (database) fingerprint spectrum may be selected as follows. Since proximity in canonical variate (CV) or principal component (PC) space is indicative of metabolic similarity, the metabolic similarity group representative that exhibits a fingerprint spectrum falling closest to the unknown's fingerprint spectrum in such spaces may be used as the transformation basis microorganism. In a particular embodiment, the raw fingerprint spectra for the metabolic similarity group representatives and the unknown are first compensated for within-session drift due to instrumental changes that occur during acquisition of the fingerprint spectra (as described in Example 4 below). The fingerprint spectra are then analyzed using a pattern recognition program (e.g. RESolve, Colorado School of Mines, Golden Colo.) and compared using a CV or PC score plot (see, for example, *Computer Assisted Bacterial Systematics*, Goodfellow et al, eds., Academic Press, London, 1985), such as a two-dimensional CV plot. The metabolic similarity group representative that is closest on the plot may be selected as the microorganism (transformation basis microorganism) on which to base the transformation that corrects for the growth medium change. The unknown's fingerprint spectrum may be transformed into its expected fingerprint spectrum using the relationship between its nearest co-analyzed neighbor's fingerprint spectrum and that neighbor's library database fingerprint spectrum. Alternatively, the unknown's fingerprint spectrum may be transformed using a vector derived from a distance-weighted average (i.e., distance in CV or PC space) of all the vectors determined between the fingerprint of the metabolic similarity group representatives co-cultured with the unknown and their library database fingerprint spectra. The weight in this case would favor those standard fingerprint spectra that are most similar to the unknown's fingerprint spectrum as judged, for example, by proximity on a score plot or by comparative Euclidean or Mahalanobis distances in CV or PC space.

The transformed fingerprint spectrum for the unknown may then be compared to spectra in the library database to identify the microorganism. This step can be done using RESolve, Statistica, Pirouette, or any other pattern recognition program, including an artificial neural network (see Example 10 below). The program makes a comparison between the pattern exhibited by the transformed fingerprint spectrum of the unknown and the patterns exhibited by fingerprint spectra for known microorganisms that are stored in the library. The unknown microorganism may be identified as being of the same type as the known microorganism exhibiting the most similar database fingerprint spectrum. Similarity may be judged, for example, by proximity of the fingerprint spectra on a CV score plot if the number of possible identities has been reduced to 4 or 5 nearest neighbors. Alternatively, similarity may be judged by algebraic and statistical methods well known in the art and embodied as standard features in available software pattern recognition packages as predictions of the likelihood of class membership.

A representative general protocol for identifying microorganisms when a culture step is used is as follows:
1. Fingerprint spectra are obtained for unknown samples that have been grown on a selective, solid medium. One small colony is sampled, so that it is probably an isolated, homogeneous colony and does not arise from a mixture of species. Other small colonies can be sampled from the same agar plate but designated as different samples not necessarily of the same strain.
2. In the same session, spectra are obtained for several samples of representative diversity and cultured ahead of time on the same media.
3. All raw spectra are compared to each other using one or more 2-D CV score plots.
4. The closest neighbor "known" is selected as an unknown's tracking reference.
5. The closest neighbor raw spectrum is used with its library spectrum to transform the unknown's raw spectrum to a corresponding database spectrum.
5(b). Alternatively, the calculation for each unknown may use a Correction Matrix derived from a distance-weighted average of all or several known raw sample spectra and their corresponding library (database) spectra.
6. Consult the database using each properly transformed spectrum to identify each unknown.

The six steps of this protocol can be executed in an automated fashion for reliable and rapid implementation using software. The concepts underlying the results discussed in Example 4 below and their interpretation suggest a second protocol that could be implemented in some situations for automated data acquisition, transformation, and sample identification in a few minutes after sampling, rather than subsequent to a 24 hour cell culture step. This second general protocol is discussed below in Example 3.

Example 2

Transformation of Fingerprint Spectra to Correct for Changes in Growth Conditions A particular embodiment of the disclosed methods is illustrated schematically in FIG. 1. Shown in the top row of FIG. 1 (database session) are three hypothetical mass spectra, one for each of three microorganisms, A, B, and C. These fingerprint spectra might, for example, represent fingerprint spectra obtained for these microorganisms under standardized conditions (e.g. grown on the same non-selective growth medium) and used as library database fingerprint spectra for the identification of these microorganisms. In the middle row (sampling session) are three hypothetical mass spectra that represent fingerprint spectra obtained for the same three microorganisms, but from a different environment (for example, grown on a different growth medium, such as a selective growth medium). These fingerprint spectra could, for example, represent the fingerprint spectra obtained for microorganisms grown on selective growth media during the early moments of an outbreak of food-borne illness. In the bottom row are fingerprint spectra that are all transformed using a relationship between the sampling session and library database session fingerprint spectra for microorganism A. Microorganism A, in this embodiment, is a representative of a metabolic similarity group within the database.

A comparison of the raw fingerprint spectra for each microorganism obtained under the two sets of conditions (sampling and database sessions, top and middle rows of FIG. 1) reveals that signals at particular masses have changed in response to the change in growth medium. In particular, a comparison of the fingerprint spectra for microorganism A reveals that the signal at mass to charge ratio (m/z)=60 has decreased, the signal at m/z=80 has increased, and the other signals have remained unchanged in response to the change in growth medium between the sampling session and the database session. Similarly, for microorganism B (which is metabolically similar to microorganism A), the signal at m/z=60 has decreased, the signal at m/z=80 is increased, and the others remain unchanged in intensity. In contrast, the changes between the sampling and database sessions for microorganism C (metabolically dissimilar to microorganism A) are in the signals at m/z=50 and m/z=90 which have decreased and increased respectively, while the signals at m/z=60, 70 and 80 remain unchanged.

The similarity of changes in the fingerprint spectra of metabolically similar microorganisms, in response to a change in growth medium, makes it possible to correctly transform the fingerprint spectra of many metabolically similar microorganisms using a transformation algorithm derived for a single representative of the group of metabolically similar microorganisms. This principle is illustrated in FIG. 1. A transformation algorithm that converts the sampling session fingerprint spectrum of microorganism A into its library database fingerprint spectrum was applied to the sampling session fingerprint spectra for microorganisms B and C. A comparison of microorganism B's transformed fingerprint spectrum (bottom row, FIG. 1) to its library database fingerprint spectrum (top row, FIG. 1) reveals that the same algorithm used to transform microorganism A's sampling session fingerprint spectrum successfully transforms microorganism B's sampling session fingerprint spectrum (middle row, FIG. 1) into its library database fingerprint spectrum. In contrast, when the algorithm is applied to transform the sampling session fingerprint spectrum of the metabolically dissimilar microorganism (microorganism C), the transformation is not successful. (In FIG. 1, compare the top row fingerprint spectrum for microorganism C to the bottom row fingerprint spectrum for the same microorganism).

In some embodiments, the transformation algorithm may be derived on an ion for ion basis (i.e., each individual ion signal appearing in a fingerprint spectrum is treated separately). For example, in FIG. 1, between the database and sampling sessions, the signal at m/z=60 for microorganism A decreases from a relative intensity of 3 to a relative intensity of 2. To transform the signal seen at m/z=60 during the sampling session back to its database intensity, the sampling session signal at m/z=60 may be multiplied by a transformation factor equal to 3/2 or 1.5. The signal at m/z=80 is seen to double in size (from relative intensity=2 to relative intensity=4) between the database and sampling sessions and its correction factor would thus be 2/4 or 0.5.

Because the signals at m/z=50, 70, and 90 are unchanged between the database and sampling sessions, the transformation factors for these ions would equal one.

Microorganism B is metabolically similar to microorganism A, and has responded to the change from sampling session growth medium to library database medium by also decreasing its production of biomolecules that yield ions of m/z=60 and increasing its production of biomolecules that yield ions of m/z=80. The transformation factors derived for microorganism A will thus correct these ion intensities in the proper direction. As seen by a comparison of the transformed and database fingerprint spectra for microorganism B, multiplying the intensities of the signals in the sampling session fingerprint spectrum of microorganism B by the same transformation factors used to transform microorganism A's fingerprint spectrum back to its library database fingerprint spectrum, successfully transforms microorganism B's sampling session fingerprint spectrum into its database session fingerprint spectrum.

In contrast, the transformation of microorganism C's fingerprint spectrum using the correction factors derived for microorganism A is unsuccessful. This is because microorganism C, being metabolically dissimilar to microorganism A, has responded to the new growth medium used for the sampling session by decreasing its production of biomolecules that yield ions of m/z=50 and increasing its production of biomolecules of m/z=90. The transformation factors derived for microorganism A (reference) for these particular ions are equal to one and therefore do not transform microorganism C's fingerprint spectrum back toward its library database fingerprint spectrum. Furthermore, the correction factors derived for microorganism A for ions of m/z=60 and m/z=80 distort the intensities of these ions in microorganism C's sampling session fingerprint spectrum when, in fact, they were unchanged between the database and sampling sessions. Thus a comparison of the transformed and library database fingerprint spectra for microorganism C reveals two very different looking spectra.

In general the type of transformation described above involves defining a correction factor at particular m/z values. At a particular m/z value, i, the correction factor, $F_i$, may be defined as $F_i = I_{i,database}/I_{i,date}$, where, $I_{i,database}$ is the relative intensity at that ion as observed in the reference spectrum from the database and $I_{i,date}$ is the corresponding value for that same microorganism's spectrum as observed on the date of analysis. The column matrix of $F_i$ values, the Correction Factor Matrix, may be matrix multiplied times the Matrix of Raw Ion Intensities of an unknown sample's spectrum. Better results are observed if the unknown's spectrum is obtained the same day and under the same culture, handling, and PyMS instrumental acquisition parameters as that date's tracking reference. The product of this process for each unknown is a Matrix of Compensated Ion Intensities, or, in other words, the unknown's compensated (corrected) spectrum.

Example 3

Identification of Microorganisms in Non-Cultured Samples

In another aspect of the disclosed methods, a microorganism of interest may be identified by its fingerprint spectrum regardless of whether it is cultured following isolation from the environment where it is found. Applying the environmental and instrumental drift compensation methods of the disclosure, identification of an unknown microorganism may be possible in as little as about one-half of an hour following its isolation. For example, microorganisms may be selectively extracted from biological fluids (e.g. urine, blood, feces, and spinal fluid) using immunoaffinity techniques and electrophoretic techniques, or impacted from aerosols, and analyzed directly to provide a fingerprint spectrum. The fingerprint spectrum may then be environmentally compensated according to the disclosed methods to provide an expected fingerprint spectrum for the microorganism in a standard database environment that may be compared to fingerprint spectra of known microorganisms in the standard database environment.

In these embodiments, identification of microorganisms is facilitated by frequently culturing, sampling, and analyzing the same set of tracking reference strains (e.g. representatives of one or more metabolic similarity groups that might otherwise be used to transform spectra following a first culture step). These fingerprint spectra are then used to transform (in reverse) the entire standard database, or a relevant subsection thereof to make a database-for-the-day. This type of transformation is actually possible with non-iterative calculations and could be executed on a personal computer in a matter of seconds, even for a large database.

Following construction of the database-for-the day, unknown microorganisms are analyzed and their spectra are transformed using tables of sample-appropriate transform vectors (or algorithms), previously determined, that provide reference microbial spectra transform vectors for each major class of non-media-cultured specimens (for example, an *E. coli* HB101 similarity type vector to transform similar samples in urine to their equivalents on TSA agar; or one for *Bacillus* samples to transform from aerosol-collected, starved cells to TSA, or one for *E. coli* 1090 similarity types to transform spectra from bacteria separated out of stool samples by immuno-affinity techniques to their correspondent spectra on TSA. The unknown microorganism's spectrum is thus transformed to its corresponding pattern had it actually been cultured on database-for-the-day media and compared to the database-for-the-day using pattern recognition for identification (e.g. subspecies-level identification).

These methods may be carried out in a clinical setting as follows. The operator of the fingerprint spectral instrument would run all the references for the day and then transform his complete reference library to a database-for-the-day (or the subset likely needed). Once a clinical sample arrives for analysis, the operator measures a fingerprint spectrum, compares its raw spectrum to the library spectra to determine the rough class to which it belongs, transforms it with the appropriate transform vector, and compares this spectrum to database-for-the-day to identify the microorganism, perhaps even before a patient leaves the clinic. Such rapid identification of microorganisms enables an attending physician to properly prescribe an antibiotic that will be effective in treating the patient.

In some embodiments, sample-appropriate transform vectors are established for a number of patient and sample types. For example, transform vectors for *E. Coli* in urine to TSA for men with urinary infections, the same for women, and for patients having a particular medical condition, such as diabetes, may be established for future reference. Such transform vectors may be established as follows:

1. Collect the type of sample from the type of patient for which rapid microbial identification is desired in the future.
2. Preserve a portion of the sample and culture another portion on a non-selective growth medium (whether or not identical to the standard database growth medium).
3. Measure the fingerprint spectra of the preserved sample, the cultured sample, and several tracking reference strains cultured on the same non-selective growth medium used to culture a portion of the collected sample.
4. Define the database-for-the-day using the tracking reference strains as described above.
5. Use the differences between the fingerprint spectrum for the preserved and cultured samples to define a transformation from raw sample to cultured sample, identify one or more metabolically similar microorganisms from the reference strains in the database-for-the-day and transform, using the differences between the reference strain's fingerprint spectrum in the database for the day and its standard database spectrum to provide, overall, a transformation algorithm (e.g. a vector in CV or PC space) for transforming spectra from the collected sample environment to the standard database environment.

These methods of identifying microorganisms from isolated and non-cultured samples are best carried out ensuring that a single type of microorganism is in the sample. Urine is a particularly attractive environment from which to isolate a single type of microorganism since it is generally sterile, except for the type microorganism causing a possible infection. In this instance, centrifugation may be sufficient to isolate the microorganism of interest. Other biological fluids (e.g. feces, saliva, sputum, pus, and blood) probably will require more extensive purification of the sample prior to analyzing a fingerprint spectrum. In these instances, immuno-affinity methods and electrophoretic (electrolytic) methods may be required. Immunological methods for isolating bacteria are disclosed, for example, in Angelo et al., "Isolation and Enrichment of *Salmonella* on Immunomagnetic Beads Prior to Detection by MALDI-TOFMS," Proceedings of the ASMS, 2001.

Example 4

Pyrolysis Mass Spectral Databases for Microbial Identification

If microorganisms are subjected to a controlled thermal degradation in an inert atmosphere or vacuum (pyrolysis), the chemical constituents that make up the cells fragment into a series of low molecular weight volatile compounds. Pyrolysis mass spectrometry is a method that measures the masses and abundances of these volatile fragments. The method involves a minimal amount of sample preparation and enables materials to be analyzed directly (i.e., without additional reagents). These attributes of the method make it relatively inexpensive and attractive for automation.

Pyrolysis mass spectrometry (PyMS) yields spectra containing a distinct fingerprint that contains sufficient chemometric information to distinguish bacterial samples even at the sub-species or strain level. (See for example, Gutteridge et al., in *Computer Assisted Bacterial Systematics,* Goodfellow et al. (eds.), Academic Press, Inc., London, pp. 369–402, 1985). It requires small amounts of sample, minimal sample preparation, and as little as three minutes for data acquisition. In many applications, a rapid comparison can be made between the PyMS spectra of samples and a limited number of authentic standards, with all culturing, sampling, data acquisition, and analysis of both unknown samples and authentic standards performed in a single session. However, this approach becomes less practical with an increasing number of possible sample identities, because the number of authentic standards that must be evaluated for comparison during the session similarly increases. An alternative approach is to build a database of fingerprint spectra for all microorganisms, or at least for those likely to be found in situations of interest. Then no authentic standards have to be run in the session as long as the distinctive PyMS fingerprint does not change substantially between sessions.

A large database can also be assembled for rapid chemotaxonomy based on PyMS spectra. To build such a database it is desirable to control and eliminate sampling, experimental, and instrumental variations that can affect the spectral patterns or to quantify and compensate for the resulting spectral distortions.

The following example illustrates methods that compensate for spectral drift due to instrumental and environmental factors (e.g. changes in growth conditions, such as changes in growth medium). It also demonstrates processes for assembling coherent PyMS library fingerprint spectral databases and consulting such databases for rapid microbial chemo-taxonomy.

Samples were cultured on TSA for 20 hours. One-millimeter colonies were sampled with a loop, and added to 400 $\mu L$ of 75% ethanol: water until the suspension was observably cloudy after sonication for approximately one minute. All PyMS spectra were collected on a Finnigan 4500 MS fitted with a Direct Exposure (wire) probe. Pyrolysis was accomplished by electrically heating 1 $\mu L$ of the suspension after it had dried onto the wire at 5 mA/sec to a maximum current of 500 mA. The PyMS spectral fingerprint of a bacterial sample was obtained with 70 eV electron impact ionization and acquired over a range of m/z 40 to 550, with averaging over 50 scans in each acquisition.

For a recently acquired *Escherichia coli* 1090 PyMS fingerprint spectrum, the relative intensity of each ion was divided into the corresponding relative intensity in a fingerprint spectrum of the same bacterium acquired two years earlier. These ratios were multiplied by corresponding intensities in both the newly acquired *E. coli* 1090 fingerprint spectra and those from several other species: *Aeromonas hydrophila,* three species of *Pseudomonas,* several *Staphylococcus* species, and others, both gram positive and gram negative.

The compensation algorithm accurately transformed the new fingerprint spectra for the test bacterium (*E. coli*) back into the old pattern (data not shown). However, the compensation algorithm did not correctly transform recent fingerprint spectra of species other than the one used to define the algorithm (also not shown). On closer examination, it was discovered that the supplier for the tryptic soy agar culture plates had changed between the early and recent samples. It appeared that differences in the chemical composition of the growth media were differentially affecting the PyMS spectra of different bacterial species. Therefore, a transformation algorithm based on the spectral drift of a single species did not transform fingerprint spectra of other bacteria where drift was due to non-instrumental experimental variability. Moreover, it was unknown whether such an algorithm would consistently transform fingerprint spectra, even for the same bacterial species, if the causes of the spectral variation were based on irreproducible culturing techniques rather than mass spectrometric instrumental drift.

Four different representative microbial species were selected to demonstrate that it is possible to correct a microorganism' spectrum for drift due to changes in culture technique if the transformation algorithm is based on changes in the spectral patterns observed for metabolically similar microorganisms. The four microbial species were *Escherichia coli, Aeromonas hydrophila,* and *Pseudomonas mendocina* (three gram-negative species) plus a mutant strain of *Staphylococcus aureus* (a gram-positive species). The bacteria were cultured on two different brands of tryptic soy agar (TSA) and on a sheep's blood agar (blood agar). All four were grown on the different growth media and then analyzed in duplicate on a single day. Analyses of microorganisms grown on Difco brand TSA were defined as the library database fingerprint spectra for these four species. Then, after the first database spectral collection, between-sessions, purely mass spectrometric drift was simulated by re-tuning and re-calibrating the mass spectrometer using a standard tune compound, PFTBA. At various dates after re-tuning and recalibrating, sessions were conducted to acquire more fingerprint spectra for: (1) *E. coli* cultured on the same (Difco brand) TSA; (2) *E. coli* cultured on Remel brand TSA, (3) *E. coli* cultured on blood agar; (4) *Aeromonas hydrophila* cultured on Difco TSA; (5) *Pseudomonas mendocino* cultured on Difco TSA; and (6) *Staphylococcus aureus* (mutant) cultured on Difco TSA. In each of these sessions, Difco TSA *E. coli* samples were analyzed at the beginning and ending of the session. These *E. coli* samples were used along with a library database (Difco TSA) *E. coli* fingerprint spectrum to perform algorithmic transformation of the other sample fingerprint spectra with respect to both within-session and between-session drift.

Transformation to correct spectral variation between a particular day's session (sampling session) and the library database session (database session) was accomplished by multiplying each sample's observed intensity at each m/z value during the sampling session by that ion's intensity for an *E. coli* standard run during the database session and dividing by the corresponding ion's intensity for an *E. coli* standard run during the sampling session. This is a between-sessions, ion-for-ion multiplicative transformation algorithm standardized by reference to *E. coli* variations observed during the sampling session.

Figure 2:
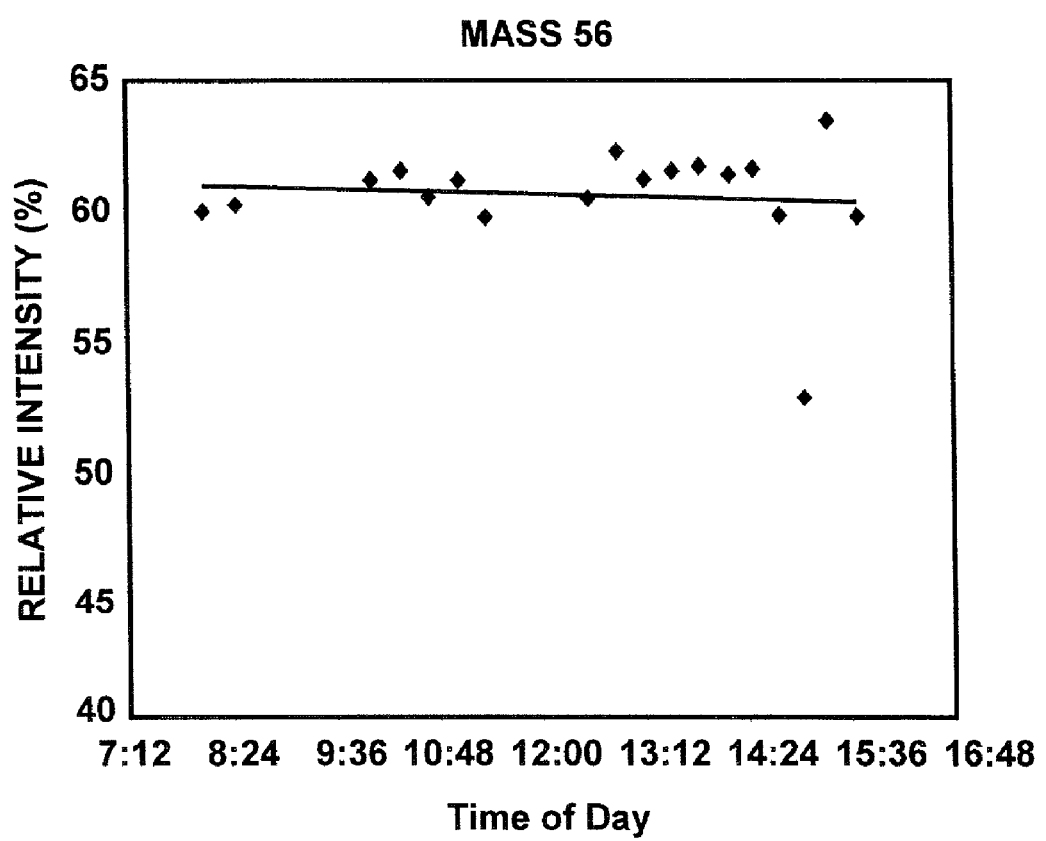
FIG. 2 is a graph showing a typical low mass relative ion intensity from a pyrolysis mass spectrum (PyMS), for multiple replicate measurements, as a function of time of day, that is as a function of the length of the session and the number of samples run on the instrument.
Figure 3:
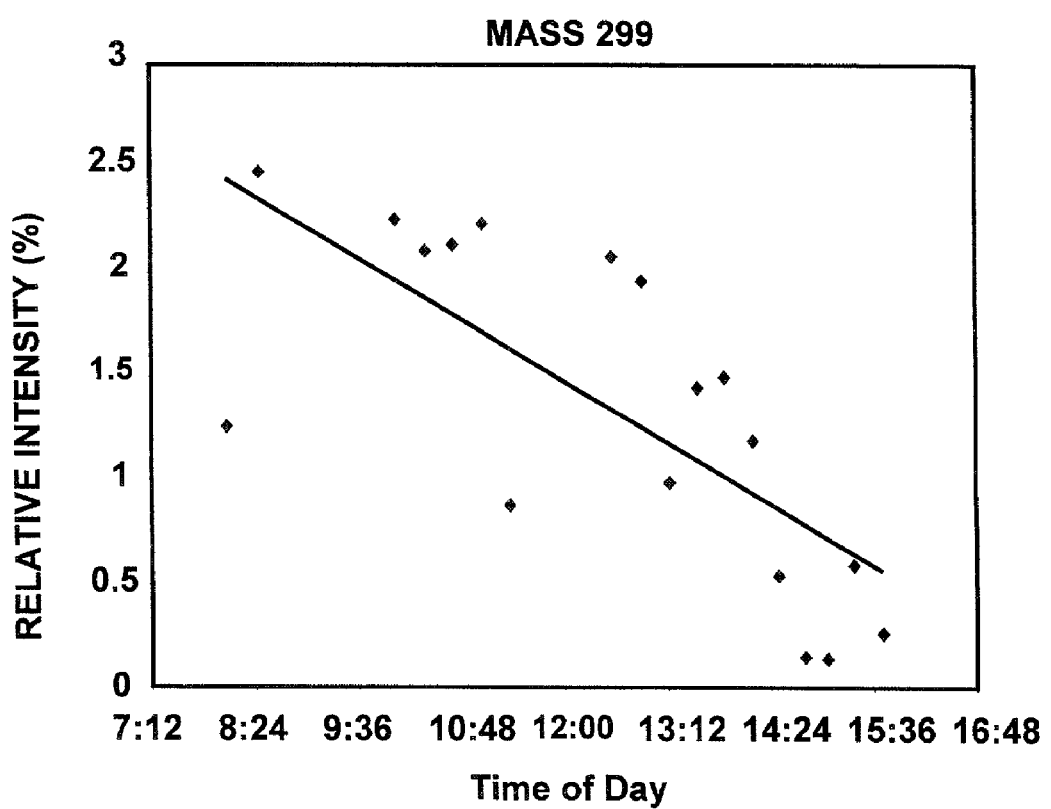
FIG. 3 is a graph showing a typical high mass relative ion intensity from a PyMS spectrum, for multiple replicate measurements, as a function of time of day, that is as a function of the length of the session and the number of samples run on the instrument.

There are other sources of spectral fingerprint variation in addition to between-sessions instrumental drift. These are called within-session drift. One cause of within-session drift is that the ion optics of a mass spectrometer tend to become contaminated with repeated sampling, leading to differential transmission efficiency for low and high mass ions. A comparison of FIG. 2 and FIG. 3 illustrates how ions of different masses may be differentially affected by ion optic contamination. The intensity for a typical high mass ion seen in the PyMS fingerprint spectrum of *E. coli* samples (m/z 299, FIG. 3) decreased, in a more-or-less linear fashion, during repeated analyses, whereas the intensity of a typical low mass ion (m/z 56, FIG. 2) remained relatively constant. Such changes lead to within-session drift of fingerprint spectral data. During the session the mass spectrometer's ion optics are becoming contaminated and the space charging that results discriminates against efficient high mass ion transmission.

Based on these observations, a within-session transformation algorithm was developed to linearly interpolate relative ion intensities based on the time of day a particular sample was analyzed. The algorithm compares the relative ion intensities for *E. coli* standards run at the beginning and end of a given sampling session and linearly interpolates relative ion intensities for intermediate times during the sampling session. For example, a sample run ⅗ths of the way through a sampling session would use, for its *E. coli* sampling session reference, a predicted fingerprint spectrum in which each relative intensity was defined as the beginning *E. coli* fingerprint spectrum's relative intensity plus ⅗ths of the difference (which may be positive or negative depending upon whether the relative intensity increased or decreased, respectively, throughout the sampling session) between the beginning and ending relative intensities. This interpolated *E coli.* fingerprint spectrum was then used as sampling session reference in the between-sessions algorithm.

Success of the within-session and between-session transformation processes was judged by the location of experimental data points on a two-dimensional canonical variate (CV) score plot. In such plots, if a between-sessions transformation is successful, the symbols for transformed fingerprint spectra of a particular bacterium will appear around or near the symbols for the database fingerprint spectra of the corresponding bacterium. Moreover, if the within-session corrections are successful, then clusters of transformed fingerprint spectra will appear tighter (i.e., less spread out on the CV score plot) than the corresponding clusters of raw fingerprint spectra from which they were transformed.

Another way to judge the success of algorithmic drift correction is by the probability that corrected spectra of known samples belong to the proper group of sample spectra in the data base.

Figure 4:
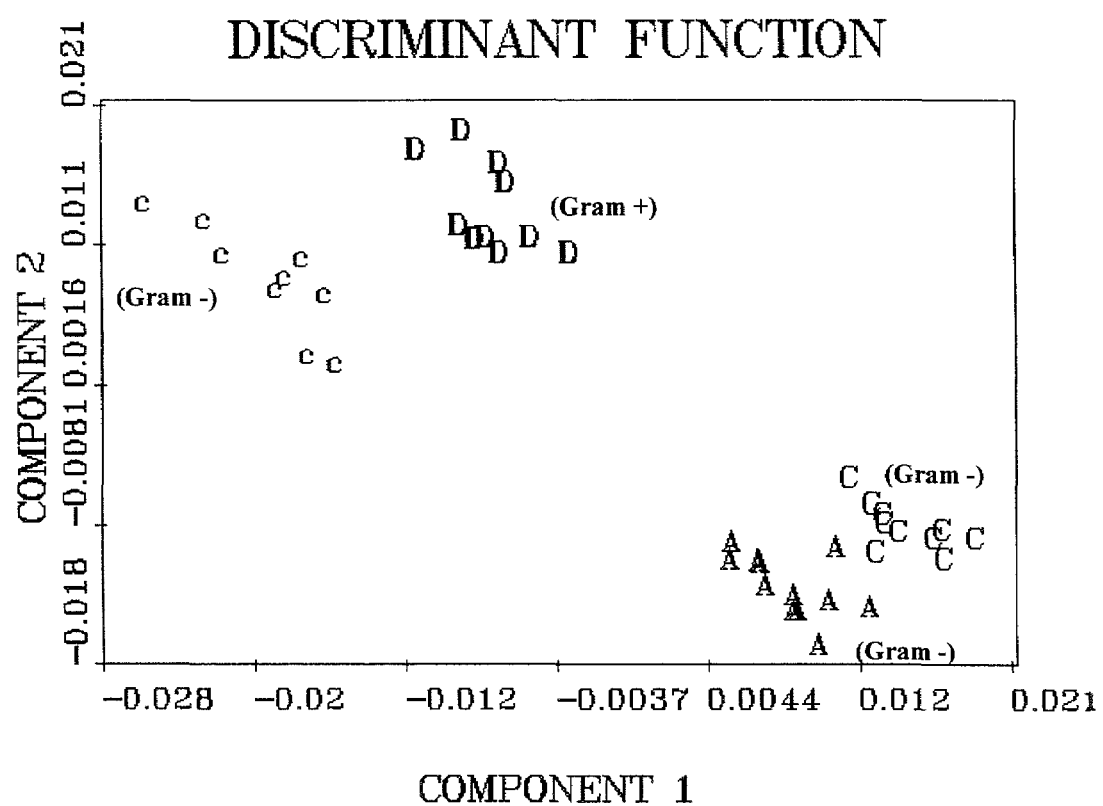
FIG. 4 is a two-dimensional canonical variate (CV) score plot (CV1 vs. CV2) for fingerprint spectra taken in a single day of four species of bacteria cultured on several growth media types.

FIG. 4 shows a two-dimensional canonical variate score plot (2-D CV score plot) for the four tested bacterial species in which all fingerprint spectra were acquired in a single session on Day 1. Even though, in this case each bacterial sample was grown on several different growth media which adversely affected the fingerprint quality, the four major types of bacterial spectra grouped into four loose but distinct clusters. FIG. 4 shows that the PyMS fingerprint spectra of *Escherichia coli* (A, gram negative) and *Aeromonas hydrophila* (C, gram negative) are more similar to each other than they are to fingerprint spectra of either *Pseudomonas mendocino* (c, also gram negative) or *Staphylococcus aureus* (D, gram positive). The proximity in score plot symbols for *Aeromonas hydrophila* and *E. coli* reflects these organism' metabolic similarity, which is reasonable since both are gram negative enterobacters. In contrast, *S. aureus* and *P. mendocina* contain quite different proportions of chemical constituents than *E. coli*, a consequence of less metabolic similarity. FIG. 4 also suggests that substantial changes in culture medium do not so distort spectra that it is impossible to score plot neighbor relationships for purposes of defining useful transform vectors. Similarly, variations in environmental experience ought not to distort a microbial PyMS spectrum so badly that it is impossible to determine from a score plot comparison or distance computation the appropriate sample transform vector to use even for an extracted, non-cultured unknown.

Figure 5:
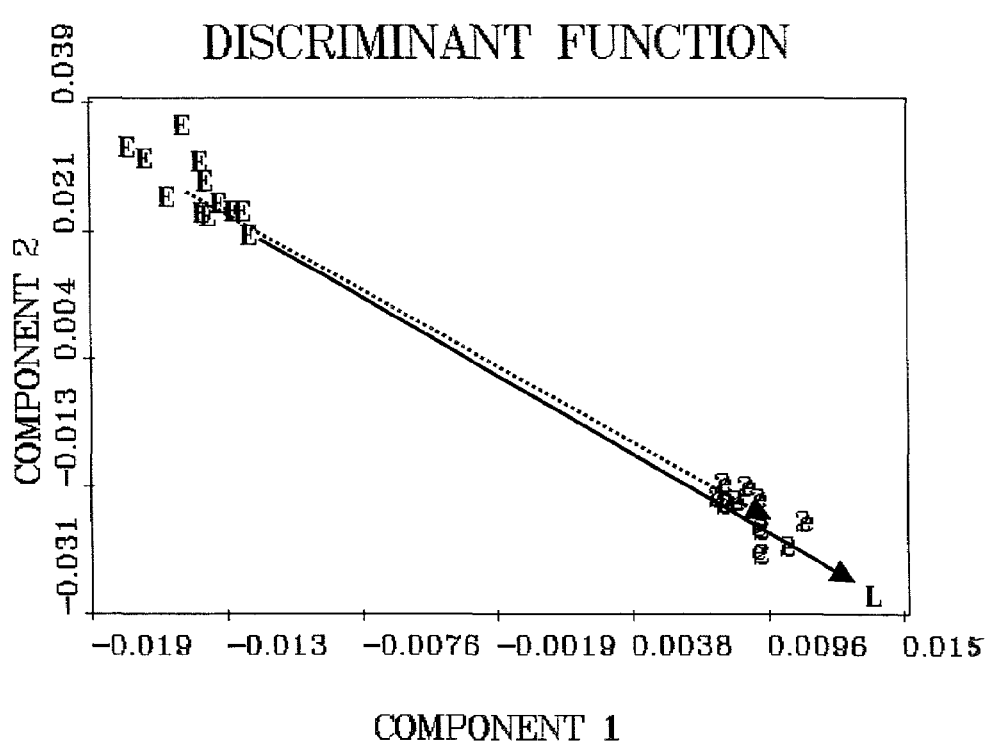
FIG. 5 is a two-dimensional canonical variate score plot (CV1 vs. CV2) showing correct mapping of fingerprint spectra for *E. Coli* grown on Difco tryptic soy agar (TSA) into the space of a Difco TSA *E. coli* database (Library) fingerprint spectrum taken four days earlier.

FIG. 5 is a 2-D CV score plot in which two slightly different algorithms have been used to transform spectra of *E. coli* grown on Difco TSA (E) from a sampling session on Day 5 (after the recalibration of the MS) back to the Difco *E. coli* Library fingerprint spectrum (L) obtained during the database session of Day 1. One of these algorithms used relative intensities for the within-session interpolation. It was observed that some of the spectra had relative intensities normalized (automatically by the mass spectrometry data acquisition program) to a different base peak than the others. In order to eliminate possible calculation anomalies and to reduce random variations in the ratios, an alternative version of the interpolation algorithm was created. The alternative version based its assessment of changes in relative ion intensity by normalizing the raw signals with respect to total ion intensity rather than the most intense peak. Symbols e and 2 in FIG. 5 represent the transformed fingerprint spectra and their clusters overlap each other because the two algorithms proved functionally equivalent. The transformed clusters are tighter than the clusters based on the raw data (E), indicating successful within-session drift correction. Also they are located very near the Library database spectrum (L) for *E. coli* grown on Difco TSA, indicating successful between-session drift correction.

Figure 6:
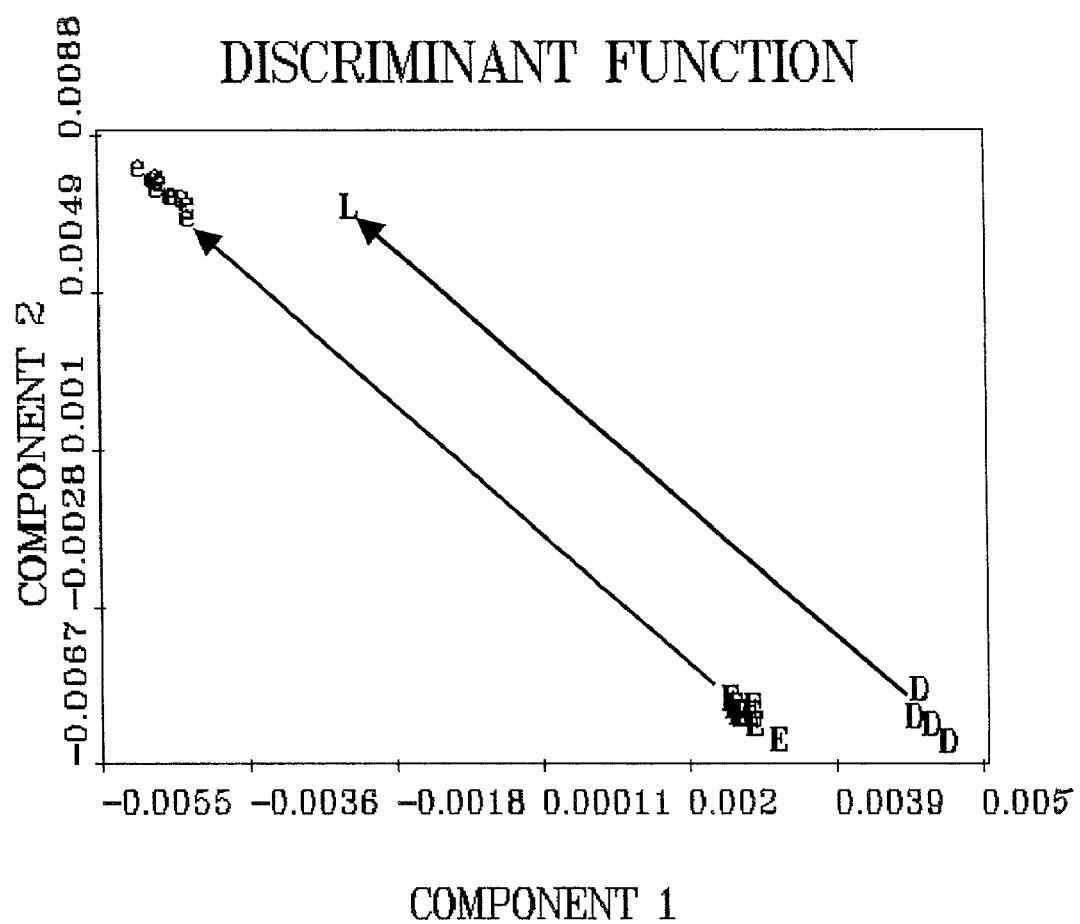
FIG. 6 is a two-dimensional canonical variate score plot (CV1 vs. CV2) showing poor mapping of fingerprint spectra for *E. coli* grown on Remel TSA into the space of a Difco TSA *E. coli* database (Library) fingerprint spectrum taken five days earlier, based on the transformation used to map Difco TSA *E. coli* fingerprint spectra to the space of the Difco TSA *E. coli* database (Library) fingerprint spectrum taken five days earlier.

FIG. 6 is a 2-D CV score plot showing how PyMS fingerprint spectra of *E. coli* grown on Remel brand TSA (E) and analyzed during a sampling session on Day 6 were transformed (e) to a location near, but not directly toward, the Difco *E. coli* Library fingerprint spectrum (L) obtained during the database session of Day 1, when the transformation (E to e) is based on the relationship (D to L) between Difco TSA grown *E. coli* from Day 6 and the Difco TSA *E. coli* Library spectrum (L) on Day 1. These results show that the transformation was not successful in correcting for between-session drift, because the Remel TSA grown *E. coli* spectrum (E) is not transformed to a point near the library, Difco TSA grown, *E. coli* (L) spectrum. Understandably, if Day 6 spectra produced by a species grown on Remel TSA are not equivalent to Day 6 Difco TSA spectra, Day 6 Remel spectra may not be correctly transformed based upon a comparison of day 6 and Library Difco TSA spectra. The mapping does not correctly compensate for a sample grown on a medium from another manufacturer even when the medium is of the same type. The algorithm lacks a reference reflecting the environmental differences between the samples.

Figure 7:
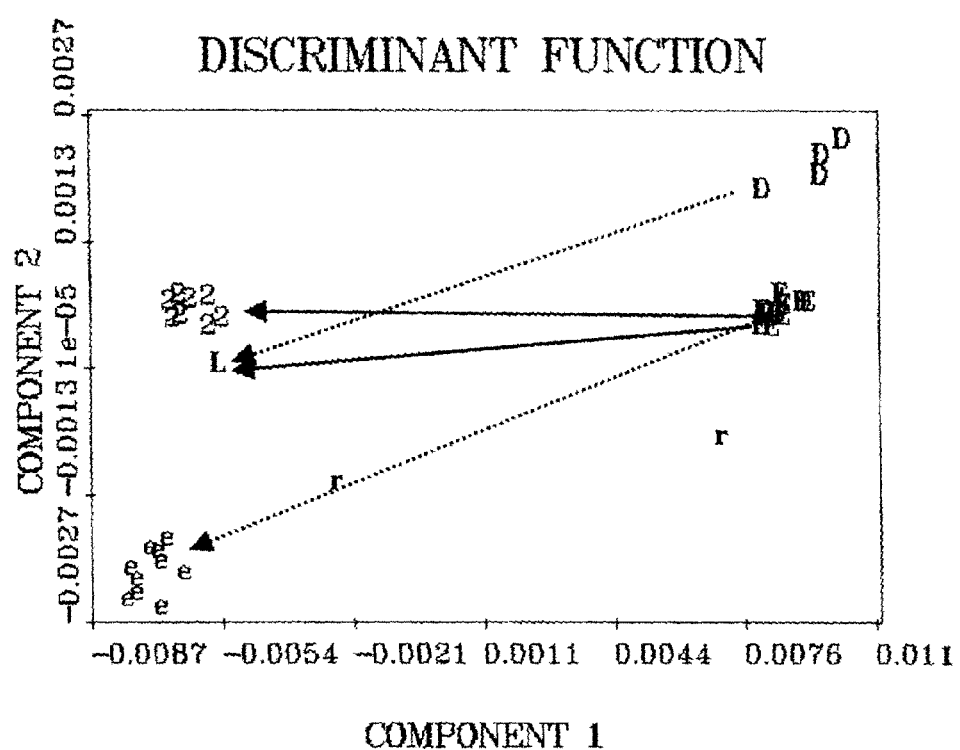
FIG. 7 is a two-dimensional canonical variate score plot (CV1 vs. CV2) showing correct mapping of fingerprint spectra for *E. coli* grown on Remel TSA into the space of a Difco *E. coli* database (Library) fingerprint spectrum taken five days earlier, based on the transformation used to map the Remel TSA *E. coli* fingerprint spectra to the Difco *E. coli* (Library) fingerprint spectrum of five days earlier.

FIG. 7 shows how using the transformation relationship (E to L) of spectra of *E. coli* grown on Remel TSA and measured during the sampling session of Day 6 (E) to the Difco TSA grown *E. coli* library fingerprint spectrum obtained during the database session of Day 1 (L), to transform (E to 2) the fingerprint spectra of Remel TSA grown *E. coli*, successfully places the corrected Remel TSA grown *E. coli* spectra (2) in a location sufficiently close to the Difco TSA library *E. coli* spectrum (L) for correct identification. The transformation relationship (E to L) was therefore successful in correcting for between-session drift due to the change in culture medium. When an appropriate reference is supplied, the algorithm compensates correctly for environmental differences.

Figure 8:
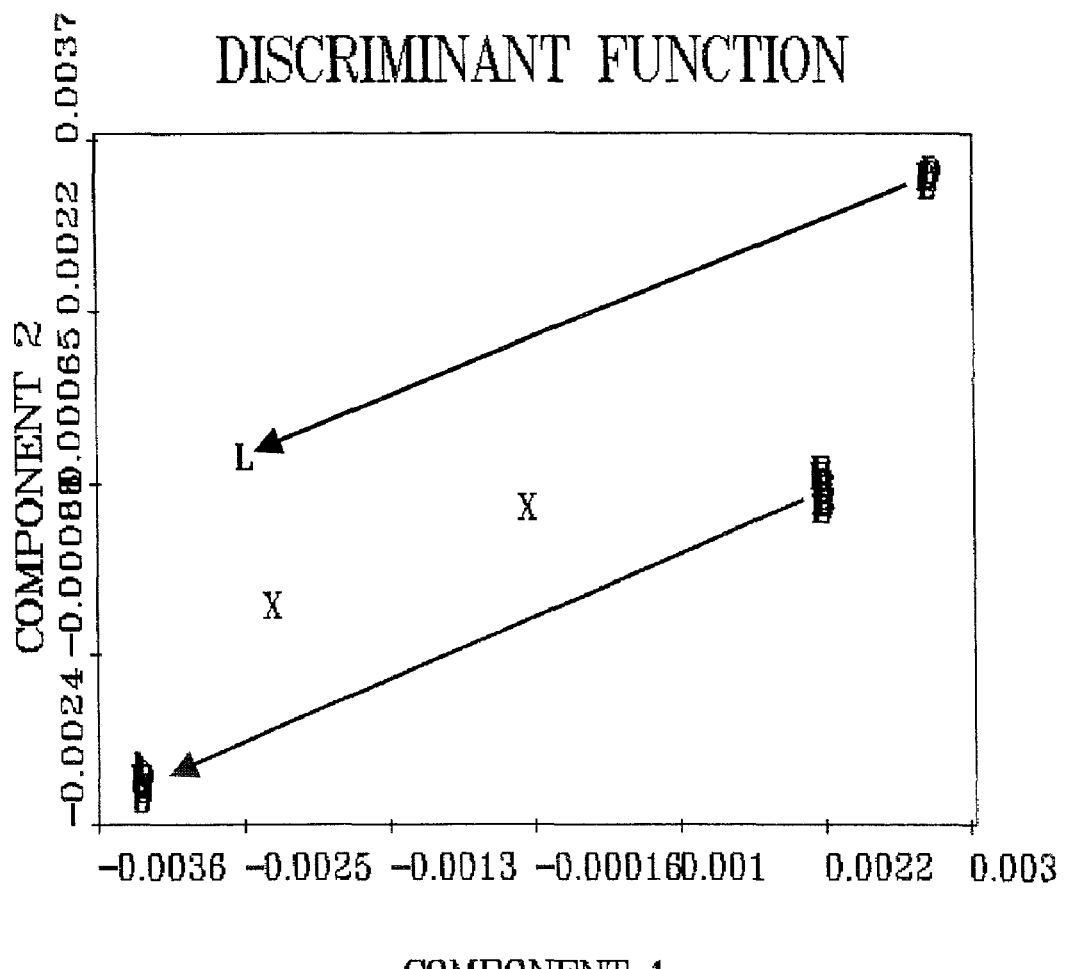
FIG. 8 is a two-dimensional canonical variate score plot (CV1 vs. CV2) showing poor mapping of fingerprint spectra for *E. coli* grown on Difco blood agar into the space of a Difco TSA *E. coli* database (Library) fingerprint spectrum of five days earlier, based on the transformation used to map the Difco TSA *E. coli* fingerprint spectra to the Difco TSA *E. coli* (Library) fingerprint spectrum of five days earlier.

FIG. 8 illustrates the failure of a Difco TSA-based transformation (D to L) when it is applied to transform (B to b) blood agar grown *E. coli* spectra from a sampling session on Day 7 (B). Not only does the transformation (D to L) fail to transform the blood agar grown spectra of *E. coli* from Day 7 (B) into the space of blood agar grown *E. coli* spectra from Day 1 (X), it does not transform the blood agar grown *E. coli* spectra of Day 7 (B) into the space of the library database session Difco TSA *E. coli* fingerprint spectrum (L). Again, if the Day 6 spectra for the same species grown on the two different growth media are not similar, an algorithm that converts the Day 6 TSA spectrum into its library equivalent is not expected to successfully convert Day 6 blood agar spectrum into the TSA library equivalent. Of course, Difco TSA between session variations cannot compensate for a fundamental difference in the type of culture medium.

Figure 9:
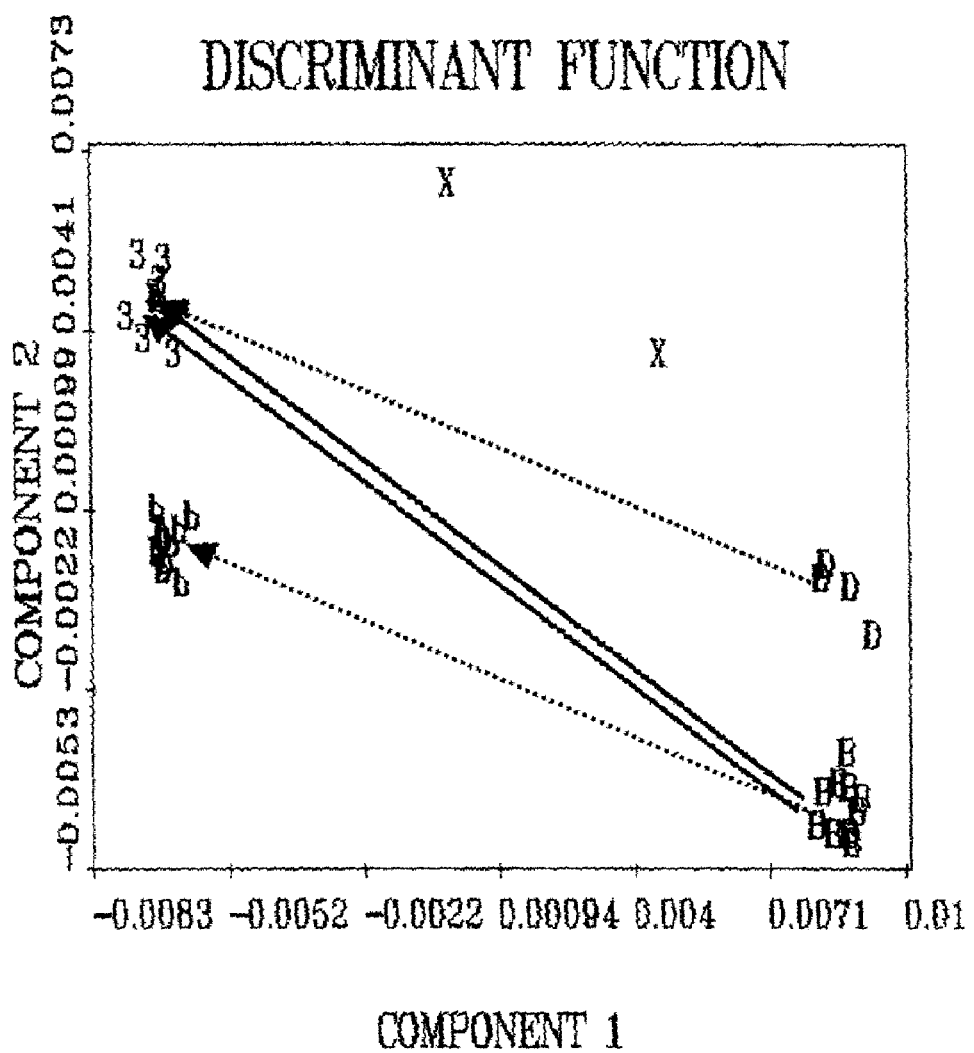
FIG. 9 is a two-dimensional canonical variate score plot (CV1 vs. CV2) showing excellent mapping of multiple fingerprint spectra for *E. coli* grown on Difco blood agar into the space of a Difco TSA *E. coli* database (Library) fingerprint spectrum obtained five days earlier, based on the transformation used to map a single Difco blood agar *E. coli* fingerprint spectrum to the Difco TSA *E. coli* (Library) fingerprint spectrum of five days earlier.

FIG. 9 shows how the transformation (B to L) between blood agar grown *E. coli* from day 7 and the library database *E. coli* fingerprint spectrum (L) can be successfully applied to blood agar grown *E. coli* spectra (B) to correctly transform (B to 3) them into the space of the Difco TSA grown library database *E. coli* fingerprint spectrum (L). These results demonstrate the ability to correct for environmental between-sessions drift due to changes in growth medium. Further, these results demonstrate the feasibility of assembling a coherent PyMS database using such transformations because they allow unknowns grown on media other than the library database medium to be identified from their fingerprint spectra after transformation to their corresponding library database growth medium spectral equivalents.

Given an appropriate reference, the transformation can compensate for instrumental and quite extensive environmental drift.

Figure 10:
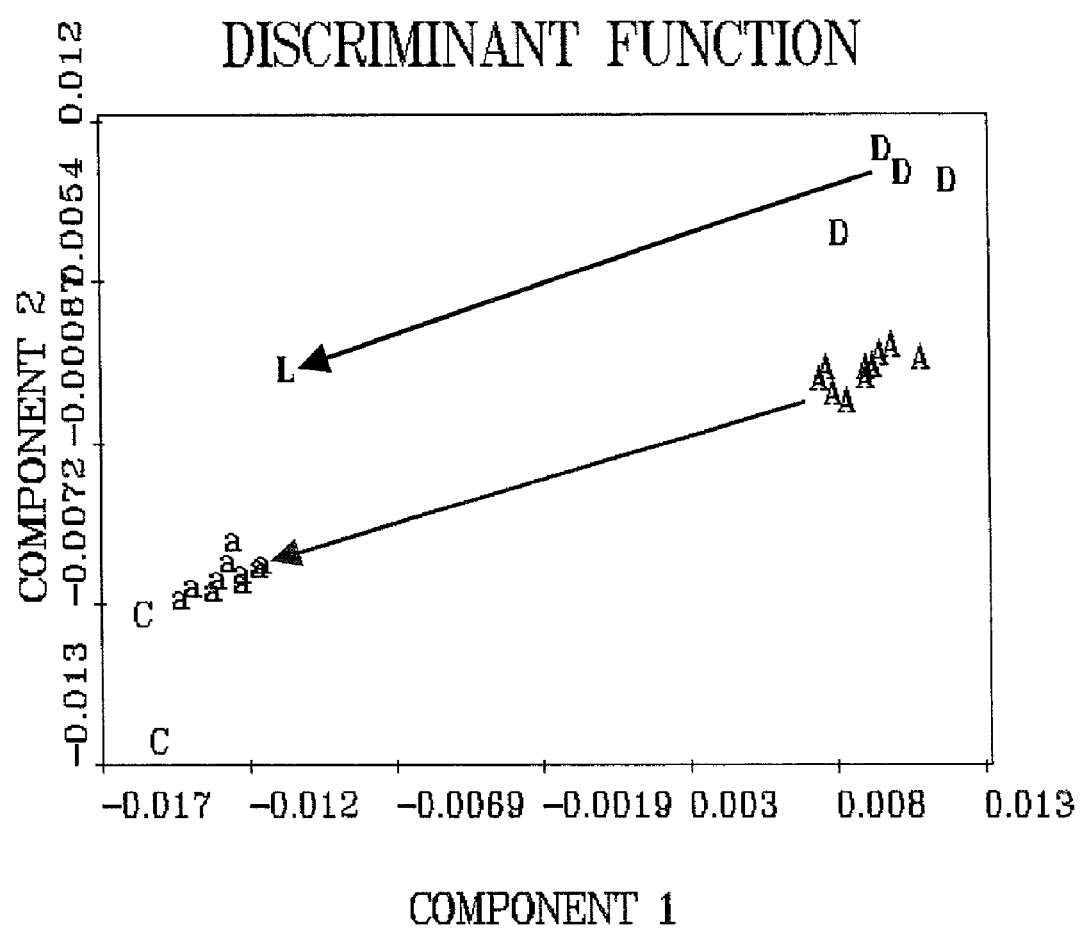
FIG. 10 is a two-dimensional canonical variate score plot (CV1 vs. CV2) showing reasonable mapping of fingerprint spectra for *A. hydrophila* grown on Difco TSA into the space of Difco TSA *A. hydrophila* library database fingerprint spectra taken six days earlier, based on the transformation used to map Difco TSA *E. coli* fingerprint spectra to the Difco TSA *E. coli* database (Library) fingerprint spectrum of six days earlier.
Figure 11:
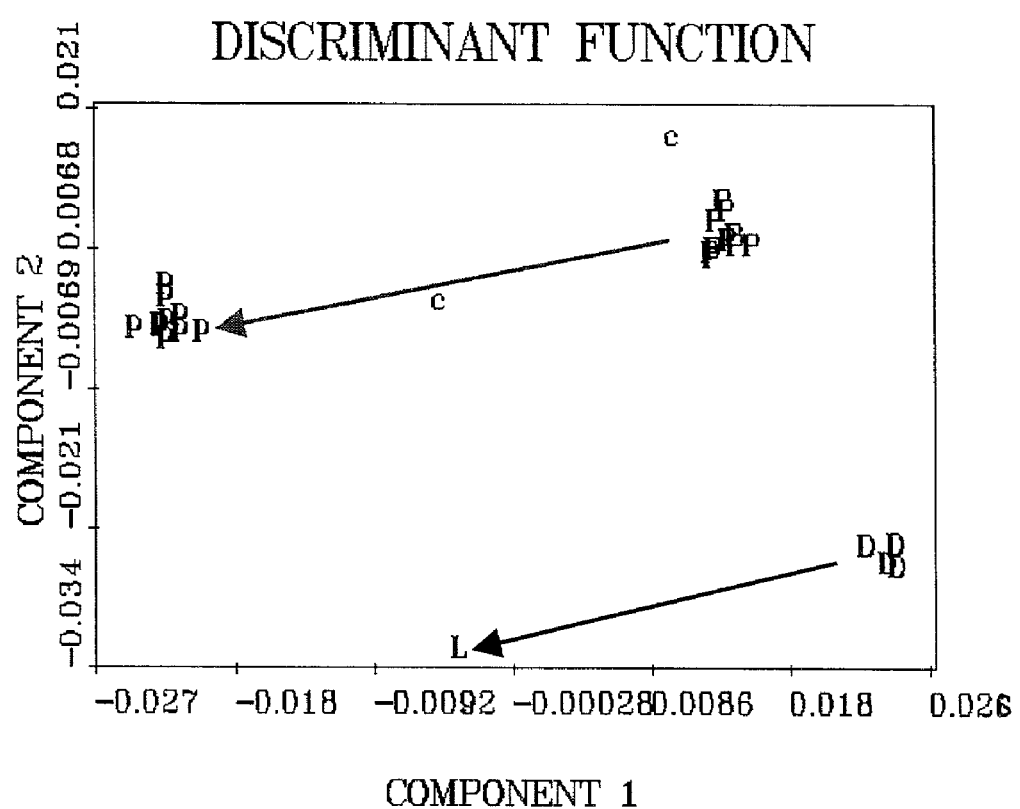
FIG. 11 is a two-dimensional canonical variate score plot (CV1 vs. CV2) showing over-compensation in mapping of fingerprint spectra for *P. mendocina* grown on Difco TSA into the space of Difco TSA *P. mendocina* database (Library) fingerprint spectra obtained six days earlier, based on the transformation used to map Difco TSA *E. coli* fingerprint spectra to the Difco TSA *E. coli* database (Library) fingerprint spectrum of six days earlier.
Figure 12:
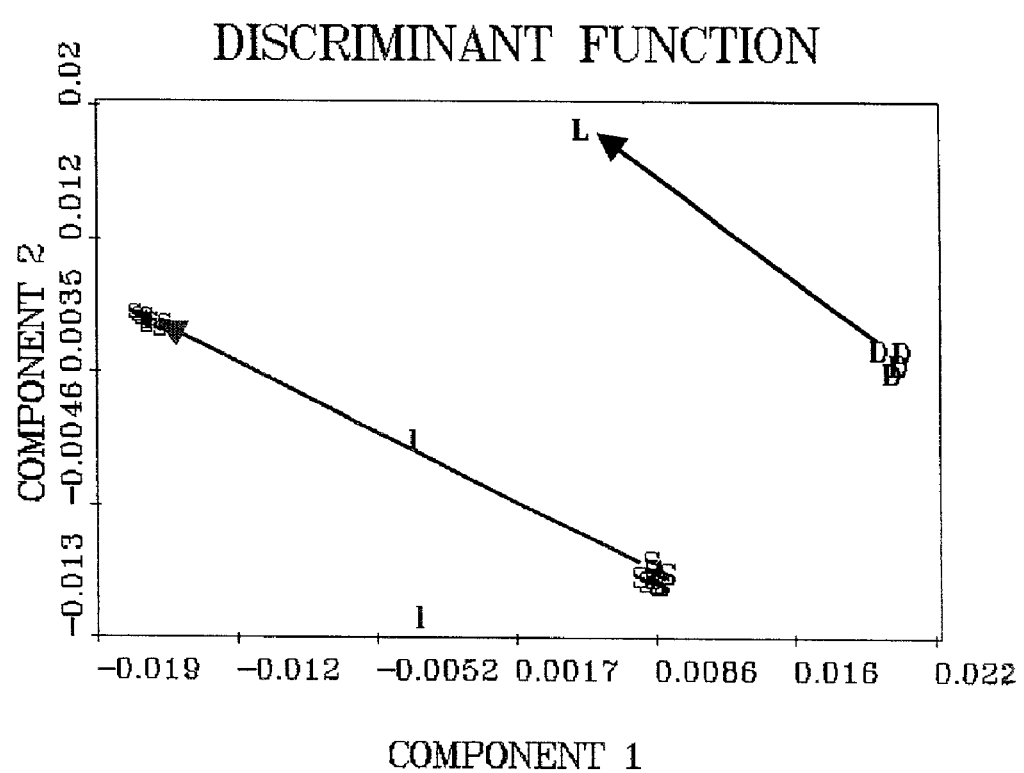
FIG. 12 is a two-dimensional canonical variate score plot (CV1 vs. CV2) showing over-compensation in mapping of fingerprint spectra for *S. aureus* grown on Difco TSA into the space of Difco TSA *S. aureus* library database fingerprint spectra obtained six days earlier, based on the transformation used to map Difco TSA *E. coli* fingerprint spectra to the Difco TSA *E. coli* library database fingerprint spectrum of six days earlier.

FIGS. 10 through 12 show the results of algorithmic transformations of fingerprint spectra of *Aeromonas hydrophila, Pseudomonas mendocina,* and *Staphylococcus aureus* species grown on Difco TSA and measured on Day 7, based upon a transformation algorithm derived from the relationship (D to L) between sampling session (Day 7, D) and library database session (Day 1, L) Difco TSA *E. coli* fingerprint spectra.

FIG. 10 shows that transformation (A to a) based on the *E. coli* reference transformation (D, Difco experimental to L, Difco library) was successful in correcting *A. hydrophila* spectra (A) to positions (a) sufficiently close to the *A. hydrophila* library database spectra (C) for identification. *E. coli* is metabolically similar to *A. hydrophila*, both being gram negative enterobacters. The success of the transformation in this instance demonstrates that fingerprint spectra of a given microorganism may be correctly transformed using a transformation algorithm based upon the relationship between two fingerprint spectra of a reference microorganism that is metabolically similar (i.e., belongs to the same metabolic similarity group). FIG. 10 also shows that an appropriate reference microorganism can be a sample of a genus different from that of the unknown sample. Note that FIG. 4 had already demonstrated the spectral and metabolic similarity of *A. hydrophila* and *E. coli*.

In contrast, FIG. 11 shows how transforming (P to p) fingerprint spectra for *Pseudomonas mendocina* from Day 7 (P) to Day 1 (p) based upon a transformation algorithm derived from the relationship (D to L) between sampling session (Day 7, D) and library database session (Day 1, L) Difco TSA *E. coli* fingerprint spectra is not successful. The transformed spectra (p) are overcompensated, being transformed in the correct direction but twice the CV score plot distance necessary for them to appear near their corresponding library database session entries (c). *Pseudomonas mendocina* (gram-negative aerobic rods) is apparently insufficiently metabolically similar to *E. coli* (gram-negative enterobacters) for the transformation to be successful. Thus, spectral compensation for species different from the reference species is not effective when the reference species are not metabolically similar to the different species. Note that FIG. 4 had already demonstrated the spectral and metabolic dissimilarity of *P. mendocina* and *E. coli*.

In FIG. 12, *Staphylococcus aureus* spectra taken on Day 7 (S) are transformed (S to s) into a position (s) on the CV score plot that does not correspond closely with the location of the *Staphylococcus aureus* library database spectrum (1). Again the transformation is based upon a transformation algorithm derived from the relationship (D to L) between sampling session (Day 7, D) and library database session (Day 1, L) *E. coli* fingerprint spectra. The transformed spectra (s) are again overcompensated, being transformed in the correct direction but twice the CV score plot distance necessary for them to appear near their corresponding library database session entries (1). Similar to *Pseudomonas mendocina, Staphylococcus aureus,* a gram-positive coccus, is apparently insufficiently metabolically similar to *E. coli* (a gram-negative enterobacter) for the transformation to be completely successful. Note that FIG. 4 had already demonstrated the spectral and metabolic dissimilarity of *S. aureus* and *E. coli*.

Attempted corrections based on inappropriate reference species appear to differ in the length but often not the direction of the transform vector. This observation may be explained by pointing out that metabolically dissimilar species contain many of the same biomolecules but in differing proportions. If the chosen reference bacterium expresses certain bioconstituents to a greater extent than the unknown sample, a correction based on its spectral variability may overestimate the magnitude of correction required for the unknown's spectrum. This does not lead to new ions or even to radical changes in relative proportion among those ions reflecting the metabolic difference. Rather, it leads to a difference in their spectral contribution relative to ions associated with unchanged constituents. This is reflected in the CV score plot with transform vectors (from dissimilar species subject to the same environmental variations) having different lengths but the same direction.

Metabolically similar organisms may be provisionally grouped by classifying organisms by two or more classification parameters, for example gram staining (e.g. gram positive or negative) and morphology (rods or cocci) or oxygen requirements (e.g. aerobic or anaerobic) or other physiological characteristics (such as ability to reduce sulfate). However a particularly convenient (although not exclusive) indication that a microorganism probably is physiologically or metabolically similar is that it is in the same genus (without necessarily being the same species).

Figure 13:
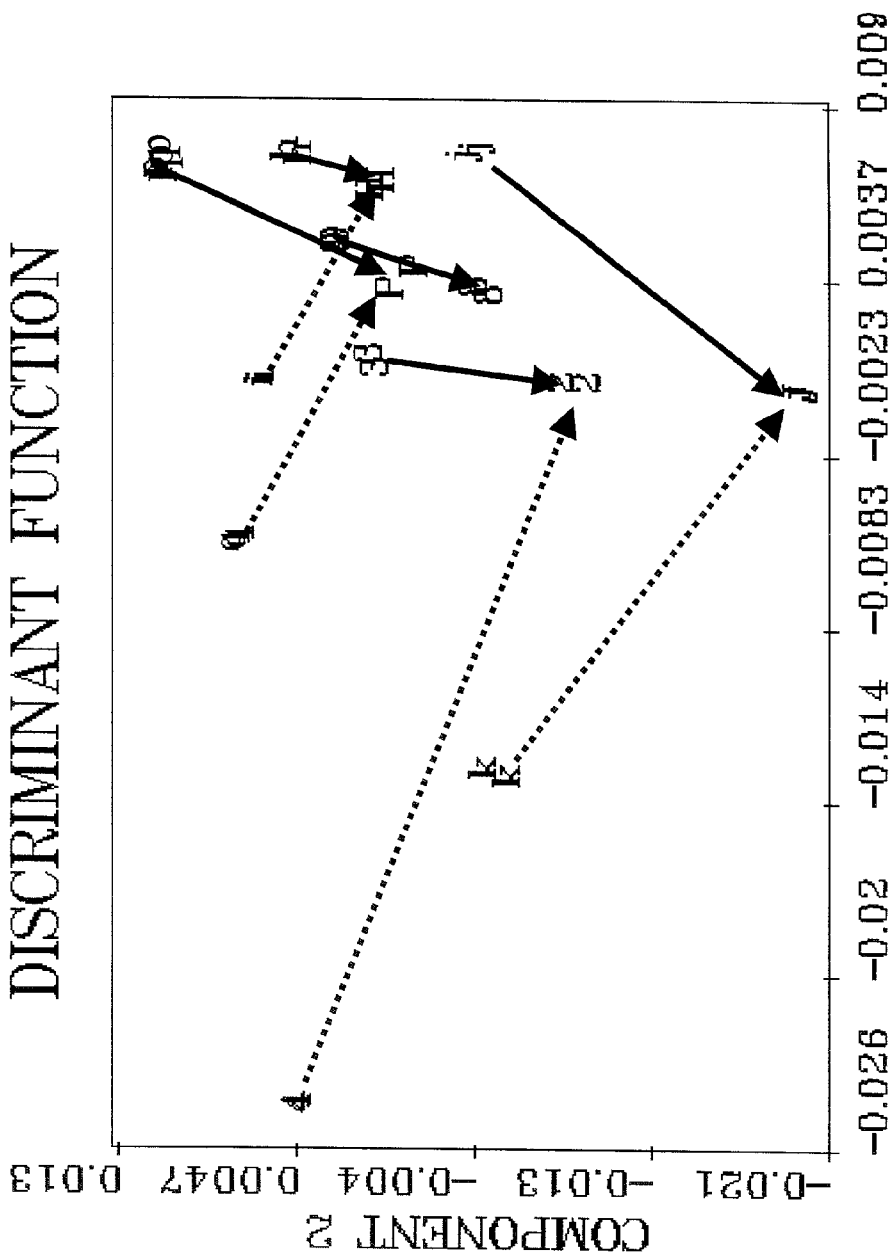
FIG. 13 is a 2-D CV score plot (CV1 vs. CV2) for 5 strains of *E. coli* grown on 3 different media showing a set of CV plot transform vectors that result from exposing the organisms to controlled environmental variations.
Figure 14:
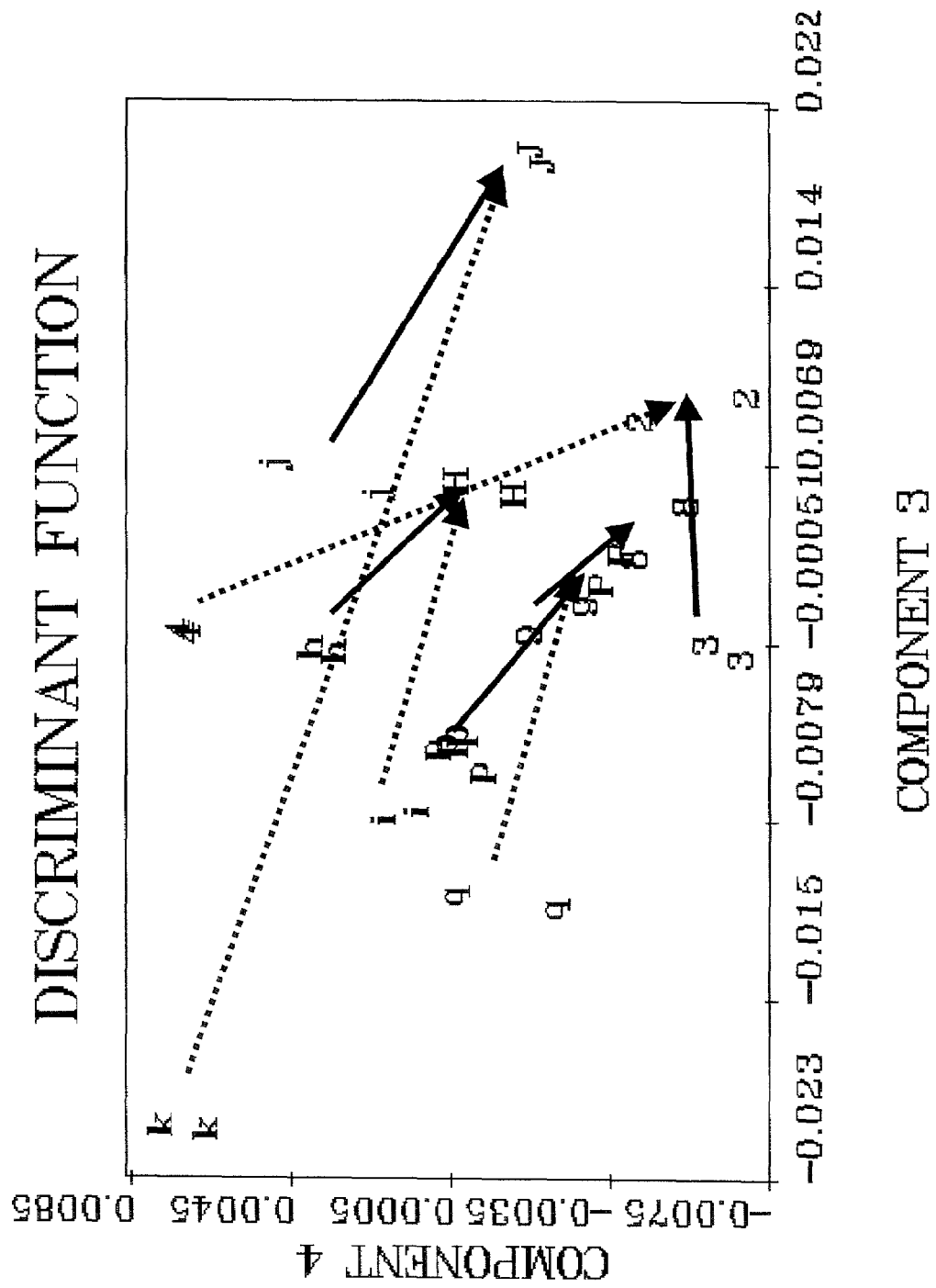
FIG. 14 is a 2-D CV score plot (CV3 vs. CV4) for 5 strains of *E. coli* grown on 3 different media showing a set of CV plot transform vectors that result from exposing the organisms to controlled environmental variations.

Metabolically similar organisms may also be identified functionally; that is, by observation and comparison of the CV plot transform vectors that result from exposing the organisms to controlled environmental variations. FIGS. 13 and 14 illustrate the results of such an experiment for 5 strains of *E. coli* grown on 3 different media. *E. coli* exist in a very large number of strains and serotypes. Some of these appear to be metabolically dissimilar. FIG. 13 shows that the relative spectral differences between culture on blood agar and TSA (shown by solid arrows) are reflected in transform vectors generally parallel to each other for these microbes, though there is some variation in CV space distances. Similarly, the relative spectral differences between MacConkey and TSA media (shown by the dashed arrows) are roughly parallel to each other but not parallel to the blood-TSA transformation vectors. A careful comparison of the relative lengths and directions of solid and dashed vectors in both FIGS. 13 and 14, leads to the conclusion that *E. coli* strains HB101 (H, h, I), PDTG112 (P, p, q) and 98222 (8, 9) are in the same metabolic similarity group whereas strains JM109 (J, j, k) and 25922 (2, 3, 4) are metabolically different both from the first three and also from each other. This example illustrates one functional method by which metabolic similarity groups may be determined.

The same data also further demonstrate the general principal that when samples grown under the same environmental conditions have spectra appearing near each other on a CV score plot, they are likely to be in the same metabolic similarity group. So, for example, in FIGS. 13 and 14, the symbols H, P, and 8 representing *E. coli* strains HB101, PDTG112, and 98222, respectively—each grown on TSA—appear near each other on both the CV1 vs. CV2 and CV3 vs. CV4 score plots. These three strains were identified as belonging to the same similarity group as assessed by their relative differential response to a variation in environmental growth conditions from TSA to either blood agar or MacConkey agar. Therefore, this data also supports the assertion discussed in detail elsewhere that one way to effect algorithmic transformation of spectra in an automated way is to define the transformation vector based on the CV space distance-weighted contributions from several nearest neighbor co-analyzed standards.

In an outbreak situation the use of one or more proximate standard spectra is the most rapid way to transform an unknown sample's spectrum for identification via the database. Later, time may be taken to verify the unknown's metabolic similarity group needed for the transformation. When constructing the database, there is time to do systematic comparative experiments such as those whose results are shown in FIGS. 13 and 14. This may not be true in an emergency. Fortunately, these results further validate the faster computer-automation-amenable approach.

The transformation will be most successful in cases where either the amount of compensation required is minimal or the reference species fingerprint spectrum (and its metabolic characteristics) is similar to that of the sample. Careful control of substantially all experimental sources of spectral variability other than species identity is best for successful database assembly. However, in cases where variations are unavoidable, selection of a reference species to track spectral variations for identifying an unknown sample would be made from those having fingerprint spectra (and metabolic characteristics) as similar as possible to that of the unknown sample.

Furthermore, for purposes of assembling a reference database of PyMS fingerprint spectra for bacterial identification, efforts would be made to eliminate random sources of spectral variation. Correction for any remaining between-session and within-session spectral variation is possible utilizing the principles demonstrated in the experiments described above (i.e., PyMS fingerprint spectra of the species used for algorithmic transformations would be metabolically similar to those of the unknown species). This requisite can be met by same-session analysis (sampling session) of freshly cultured, known samples whose fingerprint spectra together span the different regions of the database CV score plot. An unknown's raw fingerprint spectrum may then be algorithmically transformed, using as internal standard the time-interpolated fingerprint spectrum of its nearest neighbor in a score plot of the session's co-analyzed reference samples. The database is then consulted using the unknown's transformed fingerprint spectrum. Such calculations can be easily automated.

In some embodiments, reference bacteria for transforming PyMS fingerprint spectra and assembling coherent databases for the rapid identification of common bacterial pathogens may be chosen from the following sets of bacteria. Each set below is an example of a group of metabolically similar organisms.

Set A: *Salmonella* spp., *E. coli* strains, *Shigella* spp., and *Yersinia enterocolitica*.

Set B: *Aeromonas* spp., *Plesiomonas* spp., and *Vibrio* spp.

Set C: *Clostridium botulinum, Clostridium perfringens,* and *Bacillus cereus*.

Set D: *Listeria* spp.

Set E: *Staphylococcus aureus* and other *Staphylococcus species*.

Set F: *Campylobacter jejuni* and other spp.

A single strain, such as a non-pathogenic strain, from each of these sets may thus be analyzed whenever unknown samples associated with a microbial outbreak are being examined and used to provide appropriate transformation algorithms for the fingerprint spectra of the unknowns.

As discussed above, set A including *E. coli*, because of its biological diversity, may need to be subdivided in order to obtain suitable transformation spectra. The results from FIGS. 13 and 14 indicated at least three distinct such groups within the species. However, the definition of an appropriate similarity group also depends on the precision of identification required. The FIGS. 13 and 14 results indicated enough similarity among the 5 tested *E. coli* strains that any of these may serve to transform the session spectrum of an unknown *E. coli* or *Aeromonas hydrophila* sample if the identification level needed is only at the species level.

The number and identity of authentic standards to be analyzed in the same session with unknown samples in an emergency identification situation may be determined by the information that typically accompanies an unknown sample. Unknown samples do not typically appear in the lab with no information. Outbreak symptoms and epidemiology usually provide clues associated with the unknown samples, clues that would be used by the analysts to specify appropriate reference samples to be cultured in the same batch with the unknowns for the first analysis. In addition, the first culture step in an emergency situation typically involves the use of a selective medium chosen to enhance the growth of suspected causative agents. For example, in a probable *Vibrio* outbreak, the patient and environmental samples would be cultured on a *Vibrio* selective medium such as TCBS. At this point a number of authentic *Vibrio* standards would also be cultured, one sample representing each metabolic similarity group that exists within that genus.

Example 5

Fatty Acid Methyl Ester (FAME) Chromatographic Database for Microbial Identification The cellular long chain fatty acid content of microorganisms is variable and gas chromatography of fatty acid methyl esters (FAMEs) derived therefrom has been extensively used in clinical microbiology as either a primary or an adjunctive means for identification of many medically important bacteria. It has also been well established that the total fatty acid composition of a microorganism is an important taxonomic characteristic and that fatty acid data can be analyzed quantitatively to provide useful taxonomic information at the species level and, in some cases, the subspecies level. (See for example, A. G. O'Donnell, "Numerical Analysis of Chemotaxonomic Data," in *Computer Assisted Bacterial Systematics,* Goodfellow et al. (eds.), Academic Press, Inc., London, pp. 403–414, 1985 and O'Donnell et al., *J. Gen. Microbiol.,* 131: 2023–2033, 1985) However, it has also been recognized that changes in growth media lead to differences in the fatty acid content of microorganisms (See A. G. O'Donnell, "Numerical Analysis of Chemotaxonomic Data," in *Computer Assisted Bacterial Systematics,* Goodfellow et al. (eds.), Academic Press, Inc., London, pp. 403–414, 1985).

Growth media induced drift in FAME chromatograms may be corrected using the methods described in Example 2 for pyrolysis mass spectra. In certain embodiments, a chromatogram of the FAMEs derived from a sample of a microorganism may be converted (manually or with aid of computer software) to a set of paired datapoints that reflect the identity (analogous to a particular mass in a mass spectrum) and the percentage of the total FAME content (analogous to the relative intensity of a mass spectral peak) for each fatty acid originally present in the sample. These data are characteristic for each type of microorganism and may be utilized for their identification. Furthermore, because metabolically similar microorganisms will respond by producing different fatty acids in response to changes in growth medium, transformations for one representative of a group of metabolically similar microorganisms may be applied to the others within the group.

Production of FAMES (and other volatile derivatives of fatty acids, sugars, and amino acids that may serve as fingerprint molecules) from microorganisms is well known in the art. In one method, whole, lyophilized cells are methanolyzed with 2 M HCl in anhydrous methanol for 24 h at 85° C. The methanolysates are dried with a stream of nitrogen gas and derivatized (to produce volatile derivatives useful for gas chromatography) in a mixture of acetonitrile and trifluoroacetic acid anhydride at 90° C. for 3 min. (Brondz and Olsen, *Oral Microbiology and Immunology*, 8: 129–133). In another method, freeze-dried whole cells (1 mg) are methanolyzed with 1 mL of 2 M hydrochloric acid in anhydrous methanol for 24 h at 95° C. The resulting methanolysate is dried with a stream of nitrogen in an ice bath and then extracted with 1 mL of n-hexane. For assessment of hydroxy fatty acids, the hydroxy groups of these acids may be derivatized with trifluouroacetic acid anhydride after evaporation of methanol. Derivatization is accomplished in 1 mL of a solution containing 1 part of trifluoroacetic acid anhydride and 3 parts acetonitrile at 90° C. for 3 min. After derivatization, this solution is diluted before gas chromatography with 1.5 mL of acetonitrile so that it contains 10% trifluoroacetic acid anhydride. (Brondz and Olsen, *Journal of Clinical Microbiology*, 29: 183–189, 1991). In yet another method, cellular lipids are extracted from dried cells (for example 25 mg of each species or strain of microorganism) suspended in 1.0 mL of water with 4.0 mL of methanol-chloroform (3:1, v/v). The extract is dried under a nitrogen stream and reacted with 10% (w/v) boron trifluoride in methanol at 100° C. for 1 h. (Itoh et al., *FEMS Microbiology Letters*, 126: 69–74, 1995). The methylated fatty acids and aldehydes are then dissolved in n-hexane, followed by gas chromatographic analysis.

Chromatography of FAMES may be performed on any number of commercially available chromatographs utilizing in some embodiments a chromatographic column specifically designed for FAME analysis. For example, Alltech Associates, Inc. (Deerfield, Ill.) offers several columns suitable for FAME analysis, including a capillary column having as its stationary phase OV-275. In one embodiment, analysis of FAMEs derived from a sample of microorganisms is analyzed on a 5890 SERIES II gas chromatograph (Hewlett-Packard, San Diego, Calif.) equipped with a flame-ionization detector connected to a JMS-SX 102 A mass spectrometer (JWOL, Tokyo, Japan). Chromatographic separation is carried out on an HRSS-10 capillary column ( )0.25 mm i.d.×50 m, film thickness of 0.25 $\mu$m,; Shinwakako, Tokyo, Japan). The chromatograph is operated under the following conditions: column temperature, from 150° C. to 190° C. at 1° C./min: injector and detector temperature, 230° C.; carrier gas, helium or nitrogen at 1.0 mL/min; sample injection, 1.0 $\mu$L as a splitless injection; ion mode, EI positive; ion source pressure, 0.15 Torr; accelerating voltage, 10 kV; ionization voltage, 30 eV; and ionization current, 300 $\mu$A. (Itoh et al., *FEMS Microbiology Letters*, 126: 69–74, 1995).

The peaks obtained are identified by comparing retention times and mass spectra with authentic fatty acids (Sigma, ST. Louis, Mo.) and synthetic aldehydes that may, for example, be prepared by the method of Valicenti and Holman, *Chem. Phys. Lipids*, 17: 389–392, 1976. In one embodiment, the individual FAMEs are quantified from their peak areas and corrected according to their relative molar responses.

A database for identification of microorganisms based upon their FAME analysis may be created by culturing previously identified microorganisms on a nonselective growth medium, such as TSA (tryptic soy agar), blood agar, or Luria-Bertani agar for bacteria. For yeast, potato dextrose, malt extract, or Sabouraud dextrose agars are suitable. Protozoa and viruses may be cultured in a particular host within their host range.

A FAME chromatogram (or a plurality of chromatograms averaged together) is obtained and the individual FAMEs are identified, quantified, and recorded as the database session for each species or strain of microorganism. A second set of authentic samples are grown on another growth medium, such as a selective growth medium, and the results of the FAME analysis on each of the strains or species are recorded as the sampling session. All of the sampling session data is transformed to the database session by multiplying the sampling session quantity of each FAME by the ratio of the database session quantity to the sampling session quantity. Principal component analysis (PCA) or another similar multivariate analysis is performed, treating the database and sampling session microorganisms as two different species. Those species or strains that have similar vectors (in factor space) between the sampling and database session results are grouped together to form a set of metabolically similar microorganisms (metabolic similarity group). One representative of each of these metabolic similarity groups is then cultured on the same growth medium as the unknown and analyzed concurrently with the unknown to yield a set of chromatographic data. The unknown microorganism's chromatographic data may be transformed to its expected library equivalent using a transformation algorithm derived for the representative of a metabolic similarity group that exhibits sampling session chromatographic data that falls closest to the unknown's sampling session chromatographic data in canonical variate or principal component space. The transformation algorithm would be derived from the closest representative's sampling session and library database chromatographic data by dividing the library database chromatographic data by the sampling session chromatographic data to yield a set of ratios. These ratios are then multiplied by the unknown's sampling session chromatographic data to yield an expected set of chromatographic data if the unknown had been cultured on the library database growth medium.

If a large number of unknown samples are run throughout the day, references representing each of the groups of metabolically similar microorganisms are analyzed at the beginning and the end of the session. Within-session instrumental drift is corrected using transformations based on the time-interpolated chromatographic data of the references as their basis. Time-interpolated chromatographic data of reference microorganisms is obtained by first subtracting the chromatographic data for each of the reference microorganisms obtained at the beginning of the sampling session from their chromatographic data obtained at the end of the sampling session to obtain a set of differences for each reference microorganism. If, for example, an unknown microorganism's fingerprint is obtained halfway through a sampling session, the differences in the reference microorganisms chromatographic data are then multiplied by 0.5 to provide a set of values for each reference microorganism. These values (which may be positive or negative) are then added to the corresponding chromatographic data from the beginning of the sampling session to yield time-interpolated chromatographic data for each of the reference microorganisms.

The library database chromatographic data of an appropriate reference microorganism (i.e. metabolically similar to the unknown) is then divided by its time-interpolated chromatographic data to yield a set of ratios. These ratios are then multiplied by the chromatographic data for the unknown to transform the unknown microorganism's chromatographic data into that expected for the unknown if it had been measured during the establishment of the library database. Expected chromatographic data for the unknown may then be compared to library database chromatographic data of known organisms to identify the unknown.

As mentioned above, there are other cellular constituents, besides fatty acids, that may be analyzed and quantified (e.g. sugars, amino acids, and other lipid components) by gas chromatography. In other embodiments such cellular constituents are determined by liquid chromatography, such as HPLC.

Example 6

Infrared Spectral Database for Microbial Identification

Infrared (IR) spectroscopy [such as FTIR, for example, diffuse reflectance FTIR spectroscopy, including attenuated total reflectance FTIR spectroscopy (ATR-FTIR)] is another fingerprinting method for microbial identification. (See for example, Sockalingum, *Cellular and Molecular Biology*, 44: 261–269, 1998 and Naumann et al, *Nature*, 351: 81–82, 1991) Infrared spectroscopy offers the advantages of being fast, does not use reagents or consumables and is not impeded by the physical state of the sample.

IR fingerprint spectra of microorganisms are characterized in the 1800–950 $cm^{-1}$ range by several distinct regions representative of the molecules that comprise the microorganism. For example, proteins provide signals in the range 1800–1480 $cm^{-1}$, with distinct bands centered at 1639 $cm^{-1}$ and 1540 $cm^{-1}$ that are due to the peptide bond and carbohydrates appear in the range of 1215–870 $cm^{-1}$ with a signal centered at 1078 $cm^{-1}$ that is assigned to the stretching vibration of phosphate groups of sugars and nucleic acids. The use of these frequency domains for the discrimination of bacteria is now well established (Helm et al., *J. Gen. Microbiol.*, 137: 69–79, 1991).

In some embodiments, IR fingerprint spectra of microorganisms are obtained by the technique of attenuated total reflectance (ATR), allowing direct recording of the fingerprint spectra of bacterial colonies. In other embodiments, a combination of an FT-IR spectrometer and a microscope equipped with an ATR objective makes it possible to record fingerprint spectra directly from microcolonies of bacteria. The IR technique is applicable to prokaryotic as well as eukaryotic cells such as yeast, fungi (of clinical or industrial origin) and parasites.

In a particular embodiment the ATR device consists of a ZnSe crystal (Specac, UK) that provides a plurality, such as 6, internal reflections at the sample. Microbial samples are spread over the whole crystal in a homogeneous manner. Fingerprint spectra are then recorded using an FT-IR spectrometer (such as the Bomem MB-100, Vannier, Quebec, Canada). Multiple interfereograms may then averaged and the fingerprint spectra are normalized (same integrated intensity) in the range of interest (1800–950 $cm^{-1}$).

Principal component analysis may also be applied to the analysis of the IR fingerprint spectra of the microorganism in the manner described above for pyrolysis mass spectra, for example, by using digitized data. In some embodiments, the spectra are treated as pairwise datapoints that include the wavenumber and the intensity at that particular frequency. Both within-session and between-session algorithmic transformations (as described above in Examples 1, 2, 3 and 4) may then be based upon database fingerprint spectra (e.g. those obtained from microorganisms grown on a library database growth medium) and sampling session fingerprint spectra (e.g. those obtained from microorganisms grown on selective growth media) of unknowns and representatives of each of the metabolic similarity groups that might appear in an unknown sample.

Because diffuse reflectance IR spectra are very instrument specific (reflection in a diffuse reflectance cell is a non-linear process that amplifies differences between individual instruments), databases for identification of microorganisms, are best assembled for each individual diffuse reflectance IR instrument system. This may be accomplished by providing database construction and consultation software with each instrument.

Example 7

Metastable Atom Bombardment (MAB) Mass Spectral Database for Microbial Identification Sub-typing of bacteria is an important capability needed to protect public health. The determination of microbiological sub-types can identify important differences that affect both the health risk from and treatment strategies associated with microbial infection. It can also be used to monitor migration or emergence patterns for rapidly mutating strains. In cases of nosocomial (hospital-incurred) infections, sub-typing capability can be used to cluster patients suffering infections due to the same microbe as a means of identifying vectors responsible for infection. Finally, the ability to accomplish sub-typing rapidly is crucial in clinical therapy, particularly to recognize strains with respect to antibiotic resistance, acid resistance, or other therapeutically significant characteristics. One technique that may be used for sub-typing of bacteria is pyrolysis mass spectrometry with metastable atom bombardment ionization.

Metastable atom bombardment (MAB) is a novel ionization method being developed for mass spectral analysis of small molecules. Ionization is accomplished by generating metastable atoms, typically from a noble gas discharge plasma, and allowing these to impact, at low kinetic energy, with neutral analyte molecules in the gas phase. The quantum mechanical transfer of energy from the metastable atom to the analyte effects ionization. Any excess energy, a constant equal to the difference between the analyte' ionization potential and the metastable atom's energy, is imparted to the resulting ion and generates a reproducible fragmentation pattern characteristic of the analyte's bond locations and strengths. The excitation energies of noble element metastable species are shown in Table 1 (Michel J. Bertrand, P. Martin, and O. Peraldi, "A New Concept in Benchtop Mass Spectrometer: MAB-Tof" Presented at PittCon 2000, New Orleans, La.).

Fragmentation energy for helium metastable ionization of methane (IP=14.5 eV) is either 19.8–14.5=5.3 eV for 90% of the ionization events or 20.6–14.5=6.1 eV in all other events. The amount of energy transferred on contact of the metastable atom with an analyte molecule always falls into one or the other of these two cases. Efficiency of the energy transfer is independent of angle of incidence, molecular orientation, temperature or any other instrumental or experimental condition.

The amount of fragmentation can be varied by using another noble gas in which the available metastable atomic states differ from helium in the amount of energy above the ground state. For example, using argon metastables, ethane (IP=12.8 eV) would be ionized with only slightly more than 1 eV excess energy and would give a mass spectrum with high relative intensity molecular ions. Ethane would not be ionized at all by krypton or xenon.

TABLE 1

Excitation Energies of Noble Gas Metastable Species

| ↓Property Gas→ | Helium | | Neon | | Argon | | Krypton | | Xenon | |
|---|---|---|---|---|---|---|---|---|---|---|
| Metastable | $^1S_0$ | $^3S_1$ | $^3P_0$ | $^3P_2$ | $^3P_0$ | $^3P_2$ | $^3P_0$ | $^3P_2$ | $^3P_0$ | $^3P_2$ |
| Energy (eV) | 20.6 | 19.8 | 16.7 | 16.6 | 11.7 | 11.5 | 10.6 | 9.9 | 9.5 | 8.3 |
| Proportion (%) | 10 | 90 | 20 | 80 | 16 | 84 | 3 | 97 | 3 | 97 |

MAB is a novel ionization method that can give soft ionization yielding true molecular ions and do so with even greater spectral reproducibility than conventional 70 eV electron ionization (EI). [See for example, M. Mousselmal, D. Faubert, M. J. Evans and M. J. Bertrand "Comparison of EI and MAB ionization for exact mass measurement" Presented at the 44th *ASMS Conference on Mass Spectrometry and Allied Topics,* Portland, Oreg., 1996; P. Mireault, D. Faubert, A. Carrier, M. Mousselmal, and M. J. Bertrand "Evaluation of MAB as a selective ion source for chromatography/mass spectrometry technique" Presented at the 44th *ASMS Conference on Mass Spectrometry and Allied Topics,* Portland, Oreg., 1996; M. Cyr, D. Faubert, M. Mousselmal, and M. J. Bertrand "Analysis of the emanations from heated polyurethane foam using MAB-MS" Presented at the 44th *ASMS Conference on Mass Spectrometry and Allied Topics,* Portland, Oreg., 1996].

The soft ionization provided by the MAB source when operated in Krypton or Xenon mode gives true molecular ions and, sometimes, a few fragment ions having reproducible relative intensities. Thus, the taxonomic information content from each biochemical constituent in a bacterium is contained in only a few ions and their intensities. This increases sensitivity by increasing signal relative to noise in the few ion signals observed or, from the opposite point of view, by reducing the distribution of chemical information into many low intensity ion signals. Since the soft ionization is not produced in either a bi-molecular gas phase charge transfer reaction, as in conventional chemical ionization, or by in situ derivatization (as described in Beverly et al, "Fatty acid analysis of beer spoiling microorganisms using pyrolysis mass spectrometry" *J. Am. Soc. Brewing Chemists* 55(2): 79–82, 1997), the resulting spectral fingerprints are both reproducible and informative.

When combined with the methods for assembling coherent databases and consulting such databases as described in the previous Examples, the technique of MAB mass spectrometry of microorganisms may be used to successfully sub-type bacteria in a rapid fashion. For strain and sub-strain identification the fingerprint spectral patterns are desirably reproducible enough to distinguish from noise any minor but consistent variations expressed in the fingerprint. Spectra obtained using MAB ionization meet this requirement because MAB results in reproducible ion fragment ratios, efficient production of true molecular ions (due to soft-ionization), and fragmentation patterns that are independent of the particular instrument or model of instrument on which the spectra are obtained. Therefore a generally applicable library database may be assembled for MAB mass spectra.

Example 8

Computer Environments for the Chemotaxonomic Methods

The chemotaxonomic methods presently disclosed may be implemented using a single computer or utilizing a distributed computing environment. The computer system may also serve to control automated data-gathering as well as perform the analysis necessary to transform fingerprint spectra to correct for within-session instrumental drift and between-session drift due to environmental factors, such as changes in growth medium. Such combinations of computer automated data collection and analysis are common and can merely be modified to perform the methods described herein.

Exemplary Distributed Computing Environment

Figure 15:
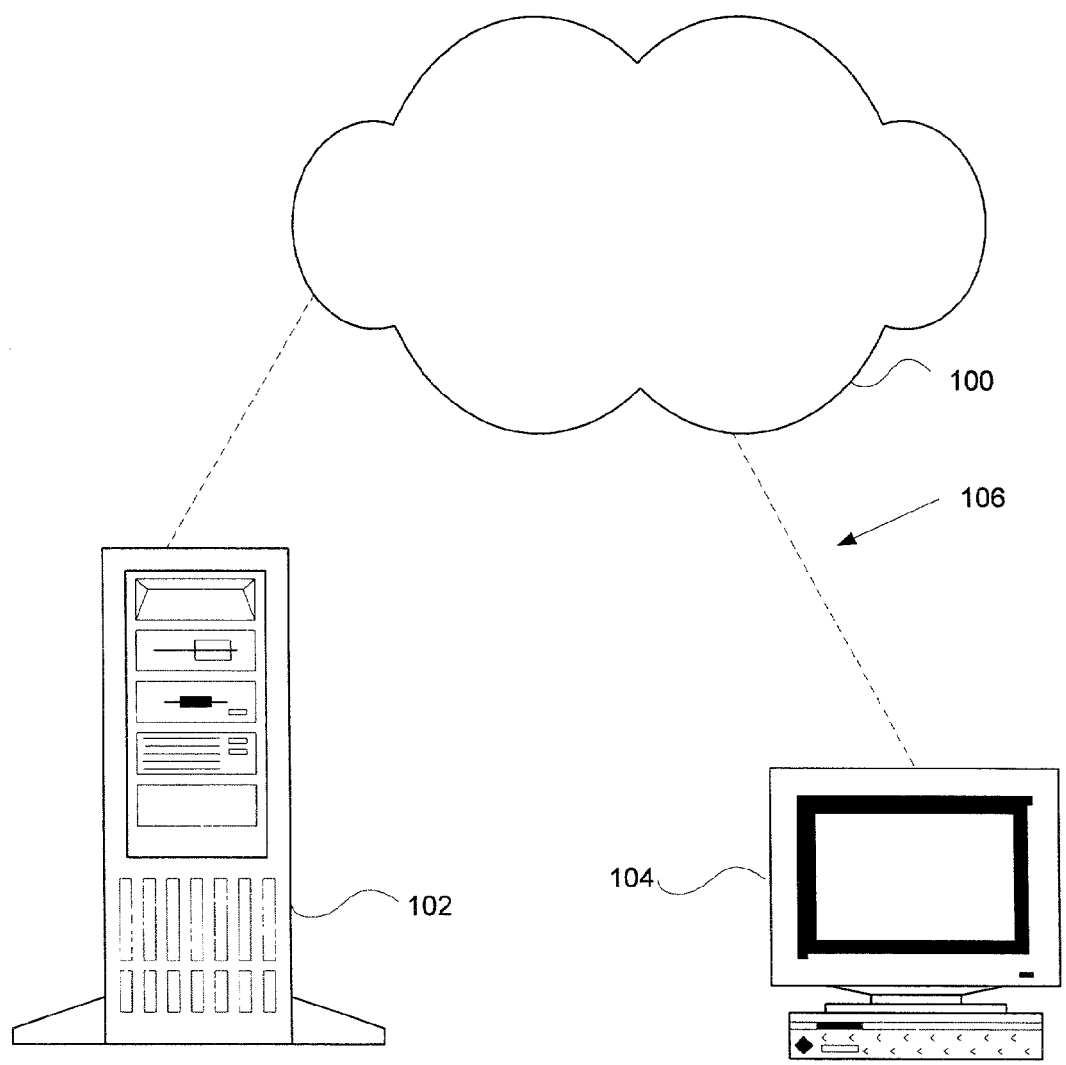
FIG. 15 is a diagram of a distributed computing environment in which the disclosed methods can be implemented.

FIG. 15 illustrates a distributed computing environment in which the software elements used to implement the disclosed methods may reside. The distributed computing environment 100 includes two computer systems 102, 104 connected by a connection medium 106. The computer systems 102, 104 can be any of several types of computer system configurations, including personal computers, multiprocessor systems, and the like. In terms of logical relation with other computer systems, a computer system can be a client, a server, a router, a peer device, or other common network node. Moreover, although FIG. 15 illustrates two computer systems 102, 104, the presently disclosed methods are equally applicable to an arbitrary, larger number of computer systems connected by the connection medium 106. Additional computer systems 102 or 104 may be connected by an arbitrary number of connection mediums 106. The connection medium 106 can comprise any local area network (LAN), wide area network (WAN), or other computer network, including but not limited to Ethernets, enterprise-wide computer networks, intranets and the Internet.

Portions of the chemotaxonomic software can be implemented in a single computer system 102 or 104, with the application later distributed to other computer systems 102, 104 in the distributed computing environment 100. Portions of the chemotaxonomic software may also be practiced in a distributed computing environment 100 where tasks are performed by a single computer system 102 or 104 acting as a remote processing device that is accessed through a communications network, with the distributed application later distributed to other computer systems in the distributed computing environment 100. In a networked environment, program modules comprising the chemotaxonomic software can be located on more than one computer system 102 or 104. Communication between the computer systems in the distributed computing network may advantageously include encryption of the communicated data.

Exemplary Computer System

Figure 16:
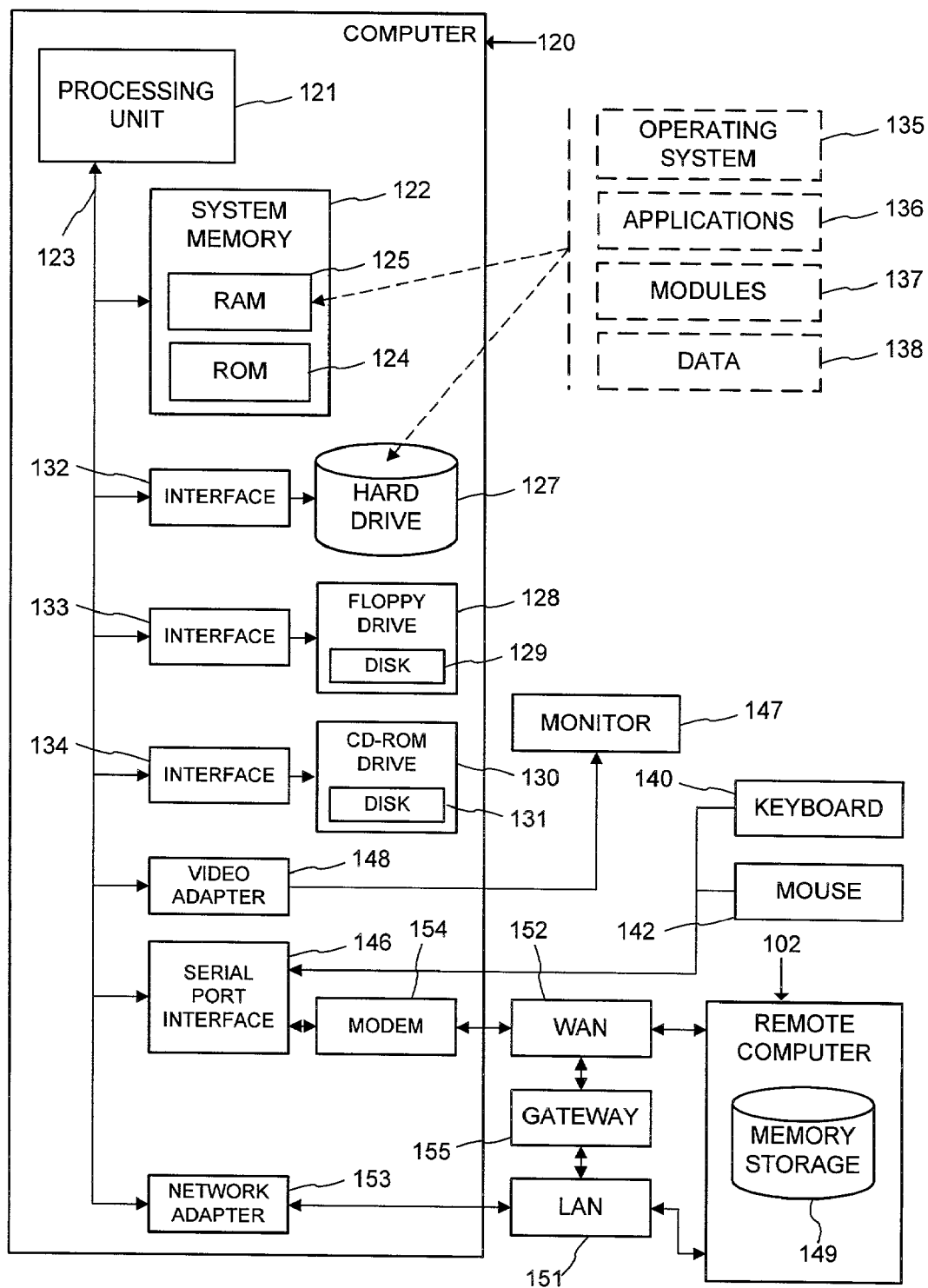
FIG. 16 is a block diagram of a computer system that can be used to implement the disclosed methods.

FIG. 16 illustrates an example of a computer system 120 that can serve as an operating environment for the chemotaxonomic software. With reference to FIG. 16 an exemplary computer system for implementing the disclosed methods includes a computer 120 (such as a personal computer, laptop, palmtop, set-top, server, mainframe, and other varieties of computer), including a processing unit 121, a system memory 122, and a system bus 123 that couples various system components including the system memory to the processing unit 121. The processing unit can be any of various commercially available processors, including Intel x86, Pentium and compatible microprocessors from Intel and others, including Cyrix, AMD and Nexgen; Alpha from Digital; MIPS from MIPS Technology, NEC, IDT, Siemens, and others; and the PowerPC from IBM and Motorola. Dual microprocessors and other multi-processor architectures also can be used as the processing unit 121.

The system bus can be any of several types of bus structure including a memory bus or memory controller, a peripheral bus, and a local bus using any of a variety of conventional bus architectures such as PCI, VESA, AGP, Microchannel, ISA and EISA, to name a few. The system memory includes read only memory (ROM) 124 and random access memory (RAM) 125. A basic input/output system (BIOS), containing the basic routines that help to transfer information between elements within the computer 120, such as during start-up, is stored in ROM 124.

The computer 120 further includes a hard disk drive 127, a magnetic disk drive 128, e.g. to read from or write to a removable disk 129, and an optical disk drive 130, e.g. for reading a CD-ROM disk 131 or to read from or write to other optical media. The hard disk drive 127, magnetic disk drive 128, and optical disk drive 130 are connected to the system bus 123 by a hard disk drive interface 132, a magnetic disk drive interface 133, and an optical drive interface 134, respectively. The drives and their associated computer-readable media provide nonvolatile storage of data, data structures, computer-executable instructions, etc. for the computer 120. Although the description of computer-readable media above refers to a hard disk, a removable magnetic disk and a CD, it should be appreciated by those skilled in the art that other types of media which are readable by a computer, such as magnetic cassettes, flash memory cards, digital video disks, Bernoulli cartridges, and the like, can also be used in the exemplary operating environment.

A number of the chemotaxonomic program modules can be stored in the drives and RAM 125, including an operating system 135, one or more application programs 136, other program modules 137, and program data 138.

A user can enter commands and information into the computer 120 through a keyboard 140 and pointing device, such as a mouse 142. Other input devices (not shown) can include a microphone, satellite dish, scanner, or the like. These and other input devices are often connected to the processing unit 121 through a serial port interface 146 that is coupled to the system bus, but can be connected by other interfaces, such as a parallel port, game port or a universal serial bus (USB). A monitor 147 or other type of display device is also connected to the system bus 123 via an interface, such as a video adapter 148. In addition to the monitor, computers typically include other peripheral output devices (not shown), such as printers.

The computer 120 can operate in a networked environment using logical connections to one or more other computer systems, such as computer 102. The other computer systems can be servers, routers, peer devices or other common network nodes, and typically include many or all of the elements described relative to the computer 120, although only a memory storage device 149 has been illustrated in FIG. 16. The logical connections depicted in FIG. 16 include a local area network (LAN) 151 and a wide area network (WAN) 152. Such networking environments are common in offices, enterprise-wide computer networks, intranets and the Internet.

When used in a LAN networking environment, the computer 120 is connected to the local network 151 through a network interface or adapter 153. When used in a WAN networking environment, the computer 120 typically includes a modem 154 or other means for establishing communications (e.g. via the LAN 151 and a gateway or proxy server 155) over the wide area network 152, such as the Internet. The modem 154, which can be internal or external, is connected to the system bus 123 via the serial port interface 146. In a networked environment, program modules depicted relative to the computer 120, or portions thereof, can be stored in the remote memory storage device. It will be appreciated that the network connections shown are exemplary and other means of establishing a communications link between the computer systems (including an Ethernet card, ISDN terminal adapter, ADSL modem, 10BaseT adapter, 100BaseT adapter, ATM adapter, or the like) can be used.

The methods, including the acts and operations they comprise, described above can be performed by the computer 120. Such acts and operations are sometimes referred to as being computer-executed. It will be appreciated that the acts and symbolically represented operations include the manipulation by the processing unit 121 of electrical signals representing data bits which causes a resulting transformation or reduction of the electrical signal representation, and the maintenance of data bits at memory locations in the memory system (including the system memory 122, hard drive 127, floppy disks 129, and CD-ROM 131) to thereby reconfigure or otherwise alter the computer system's operation, as well as other processing of signals. The memory locations where data bits are maintained are physical locations that have particular electrical, magnetic, or optical properties corresponding to the data bits.

Example 9

Other Instrumental and Non-Instrumental Fingerprint Data

In some embodiments other instrumental and non-instrumental methods may be utilized to either provide fingerprint spectra (including chromatograms) or assist in the identification of bacteria. Instrumental methods that can provide fingerprint spectra include ion mobility spectrometry (a rapid technique similar to time-of-flight mass spectrometry) and nuclear magnetic resonance spectroscopy (such as $^{1}$H, $^{13}$C, $^{15}$N, $^{19}$F, and $^{31}$P nuclear magnetic resonance spectroscopy).

As an example, an ion mobility spectral database may be constructed for the identification of prions, for which the only medically significant distinction is of protein conformation. Since there is at this time no reliable way to culture prions (a situation that is also true for many viruses and some bacteria) the disclosed spectral compensation methods may be applied using reference materials that are collected, filtered, or concentrated by the same method in comparison to library spectra that are collected, filtered, or concentrated under similar (but not identical) conditions. In addition to serving as fingerprint spectra, NMR spectra of extracts, such as extracts from bacterial cells, may be analyzed to detect the presence of low concentrations of certain cellular components, for example components produced by bacteria in response to metabolic stress, amongst other components found in high concentrations. (See for example, F. E. Evans and G. M. Hanna, "Advances in NMR Spectroscopic Techniques for Analysis of Drug Purity and the Direct Regulatory Implications from Study of the Drug Substance Genistein," 1997 FDA Forum on Regulatory Sciences, Bethesda, Md., Dec. 8–9, 1997, Poster A18 and F. E. Evans and G. M. Hanna, "NMR Analysis of Drug Purity," 111$^{th}$ AOAC International Annual Meeting and Exposition, San Diego, Calif., Sept. 7–11, 1997) The presence of cellular components in response to a particular type of stress may further indicate the metabolic similarity of two microorganisms.

Many non-instrumental methods for classifying bacteria based upon their metabolic characteristics are known. (See generally, *Bergey's Manual of Determinative Bacteriology*, 9$^{th}$ ed., Williams and Wilkins, Baltimore, Md., 1994) Example of such methods include lysis kinetics, methylene blue reduction and API test kit (Biomerieux, Lyon, France) assessment of whole cells and outer membrane vesicles and fragments. Such techniques may supply additional classification parameters useful for identifying metabolically similar microorganisms that may be utilized as references for particular groups of microorganisms.

Example 10

Pattern Recognition Methods

Pattern recognition programs useful for practicing the disclosed methods are of two major types; statistical and artificial intelligence.

Statistical methods include Principal Component Analysis (PCA) and variations of PCA such as linear regression analysis, cluster analysis, canonical variates, and discriminant analysis, soft independent models of class analogy (SIMCA), expert systems, and auto spin (see, for example, Harrington, *RESolve Software Manual*, Colorado School of Mines, 1988, incorporated by reference). Other examples of statistical analysis software available for principal-component-based methods include SPSS (SPSS Inc., Chicago, Ill.), JMP (SAS Inc., Cary N.C.), Stata (Stata Inc., College Station, Tex.), SIRIUS (Pattern Recognition Systems Ltd., Bergen, Norway) and Cluster (available to run from entropy: ~dblank/public_html/cluster).

Artificial intelligence methods include neural networks and fuzzy logic. Neural networks may be one-layer or multilayer in architecture (See, for example, Zupan and Gasteiger, *Neural Networks for Chemists*, VCH, 1993, incorporated herein by reference). Examples of one-layer networks include Hopfield networks, Adaptive Bidirectional Associative Memory (ABAM), and Kohonen Networks. Examples of Multilayer Networks include those that learn by counter-propagation and back-propagation of error. Artificial neural network software is available from, among other sources, Neurodimension, Inc., Gainesville, Fla. (Neurosolutions) and The Mathworks, Inc., Natick, Mass. (MATLAB Neural Network Toolbox).

The technique of principal component analysis (PCA) and related techniques consist of a series of linear transformations of the original m-dimensional observation vector (e.g. the mass spectrum of microorganism consisting of the ion masses and intensities) into a new vector of principal components (or, for example, canonical variates), that is a vector in principal component factor space (or, for example, canonical variate factor space). Three consequences of this type of transformation are of importance in chemotaxonomic studies. First, although a maximum of m principal axes exist, it is generally possible to explain a major portion of the variance between microorganisms with fewer axes. Second, the principal axes are mutually orthogonal and hence the principal components are uncorrelated. This greatly reduces the number of parameters necessary to explain the relationships between samples. Third, the total variance of the samples is unchanged by the transformation to Principal Components. Similarly, for canonical variates, which are orthogonal linear combinations of the PCs, the total variance remaining in those PCs selected for use is unchanged by the transformation. In the CVs it is partitioned in such a way that variance between groups of samples is maximized and variance within groups of samples is minimized. Further discussion of this method and related methods may be found, for example, in Kramer, R., *Chemometric Techniques for Quantitative Analysis*, Marcel Dekker, Inc., 1998.

Score plots are a way of visualizing the results of PCA and related techniques such as CV analysis. A sample's PC or CV score is its co-ordinate in the direction in PC or CV space defined by that particular PC or CV. A 2-dimensional PC or CV score plot shows the location of each sample projected onto the plane of the selected pair of PCs or CVs. Since there are typically fewer CVs than PCs, a CV score plot will locate the samples with less of the variance remaining in other orthogonal dimensions. Therefore, compared to a PC score plot, a CV score plot generally gives a better representation of how similar or different sample spectra are from each other. If a set of spectra are compared which only include 3 different groups, the maximum number of CVs that can be calculated is 2. In that case, the 2-D score plot of CV1 vs. CV2 incorporates all of the available variance in a single view. It may be true that, with a few more groups in which the spectra vary in "parallel"—perhaps a total of 6 groups, that the first two CVs are also sufficient for comparing spectral variance as in the methods disclosed.

Principal Component Analysis (PCA) and variations of PCA such as linear regression analysis, cluster analysis, canonical variates, and discriminant analysis, soft independent models of class analogy (SIMCA), expert systems, and auto spin may be performed utilizing the statistical program, RESolve 1.2 (Colorado School of Mines). Further discussion of PCA and its variants may be found in Harrington, *RESolve Software Manual*, Colorado School of Mines, 1988, which is incorporated herein by reference.

Pattern recognition may be performed (for example to compare transformed fingerprint to fingerprint spectra in a library database of such fingerprint spectra or to determine the similarity of vectors connecting fingerprint spectra on a score plot) using multivariate methods, such as those performed by the programs above or by any number of artificial neural network techniques. Artificial neural network software is available from, among other sources, Neurodimension, Inc., Gainesville, Fla. (Neurosolutions) and The Mathworks, Inc., Natick, Mass. (MATLAB Neural Network Toolbox).

In view of the many possible embodiments to which the principles of the disclosed methods may be applied, it should be recognized that the illustrated embodiments are only particular examples of the disclosed methods, and should not be taken as a limitation on their scope. Rather, their scope is defined by the following claims, and includes all that comes within the scope and spirit of these claims.

We claim:

1. A method for compensating for drift in fingerprint spectra due to differences in environmental factors that affect the metabolic state of microorganisms, wherein the fingerprint spectra are selected from the group consisting of mass spectra, infrared spectra, ion-mobility spectra, gas chromatograms, liquid chromatograms, and nuclear magnetic resonance spectra, and portions and combinations therefor—thereof, comprising:

culturing under a first set of environmental factors a first microorganism and a second microorganism that is presumably metabolically similar to the first microorganism; wherein metabolically similar microorganisms are organisms that exhibit similar fingerprint spectra that change similarly in response to changes in the environment;

measuring a fingerprint spectrum of the first microorganism cultured under the first set of environmental factors and a fingerprint spectrum of the second microorganism cultured under the first set of environmental factors;

obtaining a fingerprint spectrum of the second microorganism cultured under a second set of environmental factors that differ from the first set of environmental factors and affect the metabolic state of the first and second microorganisms;

deriving a relationship between the fingerprint spectrum of the second microorganism cultured under the first set of environmental factors and the fingerprint spectrum of the second microorganism cultured under the second set of environmental factors; and, applying the relationship derived for the second microorganism to transform the fingerprint spectrum of the first microorganism cultured under the first set of environmental factors to an expected fingerprint spectrum for the first microorganism under the second set of environmental factors that is compensated for drift due to the differences between the first and second sets of environmental factors that affect the metabolic state of the first microorganism.

2. The method of claim 1, wherein culturing under a first set of environmental factors comprises culturing on a test growth medium and culturing under the second set of environmental factors comprises culturing on a library growth medium that differs from the test growth medium.

3. The method of claim 1 further including a step of identifying the first microorganism by detecting a similarity between the expected fingerprint spectrum for the second microorganism and a fingerprint spectrum of a known organism cultured under the second set of environmental factors.

4. The method of claim 3, wherein detecting a similarity is accomplished by a pattern recognition method selected from the group consisting of statistical pattern recognition methods, artificial intelligence pattern recognition methods, and combinations thereof.

5. The method of claim 1, wherein the derived relationship comprises proportional differences in individual elements of the fingerprint spectra of the second microorganism between the first and second sets of environmental factors.

6. The method of claim 1, wherein the first microorganism is presumed to be a bacterium belonging to a certain class of physiologically similar bacteria and the second, presumably metabolically similar microorganism belongs to the same class of physiologically similar bacteria, but the first and second microorganisms belong to different genera of bacteria of the same class of physiologically similar bacteria.

7. The method of claim 1, wherein the first microorganism is presumed to be a bacterium belonging to a certain genus of bacteria and the second, presumably metabolically similar microorganism is of the same genus of bacteria, but the first and second microorganisms belong to different species of bacteria of the same genus of bacteria.

8. The method of claim 1, wherein the first microorganism is presumed to be a bacterium belonging to a certain species of bacteria and the second, presumably metabolically similar microorganism is of the same species of bacteria, but the first and second microorganisms belong to different strains of the same species of bacteria.

9. The method of claim 1, wherein the second, presumably metabolically similar microorganism is a representative of a metabolic similarity group that exhibits a fingerprint spectrum that is closest in canonical variate or principal component space to the fingerprint spectrum exhibited by the first microorganism under the first set of environmental conditions.

10. The method of claim 9, wherein the second, presumably metabolically similar microorganism is a distance-weighted composite of two or more representatives of metabolic similarity groups.

11. The method of claim 1, wherein the first set of environmental factors and the second set of environmental factors comprise the same batch of the same growth medium and the first set of environmental factors and the second set of environmental factors differ in at least one parameter selected from the group consisting of temperature, pressure, exposure to light, and exposure to gases.

12. The method of claim 1, wherein the method is computer implemented.

13. The method of claim 1, wherein the first and second sets of environmental factors comprise different growth media.

14. The method of claim 1, wherein the first and second sets of environmental factors comprise two batches of the same type of growth media.

15. The method of claim 1, wherein the fingerprint spectra are pyrolysis mass spectra.

16. The method of claim 1 further comprising adding the expected spectrum of the first microorganism to a database.

17. The method of claim 11, wherein the first and second sets of environmental factors differ in temperature.

18. A method for compensating for drift in fingerprint spectra due to differences in environmental factors that affect the metabolic state of microorganisms, wherein the fingerprint spectra are selected from the group consisting of mass spectra, electron impact mass spectra, pyrolysis mass spectra, MAB mass spectra, MALDI mass spectra, ESI mass spectra, infrared spectra, Fourier-transform infrared spectra, diffuse reflectance infrared spectra, attenuated total reflectance infrared spectra, ion-mobility spectra, gas chromatograms, fatty-acid methyl ester gas chromatograms, liquid chromatograms, and nuclear magnetic resonance spectra, and portions and combinations thereof, comprising:

culturing under a first set of environmental factors a first microorganism and a second microorganism that is presumably metabolically similar to the first microorganism; wherein metabolically similar microorganisms are organisms that exhibit similar fingerprint spectra that change similarly in response to changes in the environment;

measuring a fingerprint spectrum of the first microorganism cultured under the first set of environmental factors and a fingerprint spectrum of the second microorganism cultured under the first set of environmental factors;

obtaining a fingerprint spectrum of the second microorganism cultured under a second set of environmental factors that differ from the first set of environmental factors and affect the metabolic state of the first and second microorganisms;

deriving a relationship between the fingerprint spectrum of the second microorganism cultured under the first set of environmental factors and the fingerprint spectrum of the second microorganism cultured under the second set of environmental factors; and, applying the relationship derived for the second microorganism to transform the fingerprint spectrum of the first microorganism cultured under the first set of environmental factors to an expected fingerprint spectrum for the first microorganism under the second set of environmental factors that is compensated for drift due to the differences between the first and second sets of environmental factors that affect the metabolic state of the first microorganism.

19. A method for compensating for drift in fingerprint spectra due to differences in environmental factors that affect the metabolic state of microorganisms, comprising:

culturing under a first set of environmental factors a first microorganism and a second microorganism that is presumably metabolically similar to the first microorganism; wherein metabolically similar microorganisms are organisms that exhibit similar fingerprint spectra that change similarly in response to changes in the environment;

measuring a pyrolysis mass spectrum of the first microorganism cultured under the first set of environmental factors and a pyrolysis mass spectrum of the second microorganism cultured under the first set of environmental factors;

obtaining a pyrolysis mass spectrum of the second microorganism cultured under a second set of environmental factors that differ from the first set of environmental factors and affect the metabolic state of the first and second microorganisms;

deriving a relationship between the pyrolysis mass spectrum of the second microorganism cultured under the first set of environmental factors and the pyrolysis mass spectrum of the second microorganism cultured under the second set of environmental factors; and, applying the relationship derived for the second microorganism to transform the pyrolysis mass spectrum of the first microorganism cultured under the first set of environmental factors to an expected pyrolysis mass spectrum for the first microorganism under the second set of environmental factors that is compensated for drift due to the differences between the first and second sets of environmental factors that affect the metabolic state of the first microorganism.

20. The method of claim 1, wherein the mass spectra are electron impact, pyrolysis, MALDI, ESI, nanospray, or MAB mass spectra.

21. The method of claim 1, wherein the infrared spectra are Fourier-transform infrared spectra, diffuse reflectance infrared spectra or attenuated total reflectance infrared spectra.

22. The method of claim 1, wherein the gas chromatograms are chromatograms of derivatized cellular fatty acids, sugars, or amino acids.

23. The method of claim 22, wherein the gas chromatograms are fatty-acid methyl ester gas chromatograms.

24. The method of claim 1, wherein the liquid chromatograms are high-performance liquid chromatograms of proteins, nucleic acids, lipids or sugars.

25. The method of claim 1, wherein the nuclear magnetic resonance spectra are $^{13}C$, $^{1}H$, $^{15}N$, $^{19}F$, $^{31}P$, or two-dimensional homonuclear or heteronuclear magnetic resonance spectra.

* * * * *

UNITED STATES PATENT AND TRADEMARK OFFICE
CERTIFICATE OF CORRECTION

PATENT NO. : 6,996,472 B2  
APPLICATION NO. : 09/975530  
DATED : February 7, 2006  
INVENTOR(S) : Wilkes et al.

Page 1 of 1

It is certified that error appears in the above-identified patent and that said Letters Patent is hereby corrected as shown below:

In the Specification:

Column 5, line 56 (specification page 10, line 20), "$^{31}$p" should be --$^{31}$P--.

Column 6, line 62 (specification page 12, line 20), "$^{31}$p" should be --$^{31}$P--.

Column 9, line 15 (specification page 16, line 24), "microorganism'" should be --microorganisms'--.

Column 21, line 57 (specification page 37, line 12), "microorganism'" should be --microorganisms'--.

Column 23, line 30 (specification page 39, line 29), "organism'" should be --organisms'--.

Column 32, line 50-51 (specification page 55, line 3), "Pit-tCon" should be --Pittcon--.

Signed and Sealed this

Tenth Day of July, 2007

JON W. DUDAS  
*Director of the United States Patent and Trademark Office*

UNITED STATES PATENT AND TRADEMARK OFFICE
CERTIFICATE OF CORRECTION

| | |
|---|---|
| PATENT NO. | : 6,996,472 B2 |
| APPLICATION NO. | : 09/975530 |
| DATED | : February 7, 2006 |
| INVENTOR(S) | : Wilkes et al. |

Page 1 of 1

It is certified that error appears in the above-identified patent and that said Letters Patent is hereby corrected as shown below:

In the Claims:

In Claim 1, (Col. 39, line 5), "therefore-thereof" should be --thereof--.

Signed and Sealed this

Twenty-first Day of August, 2007

JON W. DUDAS
*Director of the United States Patent and Trademark Office*